(12) United States Patent
Tampieri et al.

(10) Patent No.: US 11,213,605 B2
(45) Date of Patent: Jan. 4, 2022

(54) LARGE 3D POROUS SCAFFOLDS MADE OF ACTIVE HYDROXYAPATITE OBTAINED BY BIOMORPHIC TRANSFORMATION OF NATURAL STRUCTURES AND PROCESS FOR OBTAINING THEM

(71) Applicant: GREENBONE ORTHO S.P.A., Faenza (IT)

(72) Inventors: Anna Tampieri, Faenza (IT); Simone Sprio, Bologna (IT); Andrea Ruffini, Bagnacavallo (IT)

(73) Assignee: GREENBONE ORTHO S.P.A., Faenz (IT)

( * ) Notice: Subject to any disclaimer, the term of this patent is extended or adjusted under 35 U.S.C. 154(b) by 0 days.

(21) Appl. No.: 16/875,554

(22) Filed: May 15, 2020

(65) Prior Publication Data
US 2020/0276356 A1    Sep. 3, 2020

Related U.S. Application Data

(62) Division of application No. 15/750,568, filed as application No. PCT/IB2016/054665 on Aug. 3, 2016, now Pat. No. 10,688,218.

(30) Foreign Application Priority Data

Aug. 6, 2015 (IT) .......................... 102015000042762
Aug. 6, 2015 (IT) .......................... 102015000042834

(51) Int. Cl.
*A61L 27/12*    (2006.01)
*A61L 27/36*    (2006.01)
*A61L 27/56*    (2006.01)

(52) U.S. Cl.
CPC .......... *A61L 27/12* (2013.01); *A61L 27/365* (2013.01); *A61L 27/3637* (2013.01); *A61L 27/56* (2013.01); *A61L 2430/02* (2013.01)

(58) Field of Classification Search
CPC .... A61L 27/12; A61L 27/3637; A61L 27/365; A61L 27/56; A61L 2430/02
See application file for complete search history.

(56) References Cited

U.S. PATENT DOCUMENTS

2006/0292350 A1    12/2006    Kawamura et al.
2014/0134258 A1     5/2014    Tampieri et al.
2014/0371869 A1    12/2014    Atala et al.

FOREIGN PATENT DOCUMENTS

| CN | 101829363 A | 9/2019 |
|---|---|---|
| JP | 200566354 A | 2/2007 |
| WO | 0162109 A1 | 8/2001 |
| WO | 2012063201 A1 | 5/2012 |

OTHER PUBLICATIONS

International Search Report and Written Opinion dated Oct. 19, 2016, from International Application No. PCT/IB2016/054665, 14 pages.
Bertinetti, et al., Punctual investigation of surface sites of HA and magnesium-HA J of the E Ceramic Society 26 2006 987-991.
Ruffini, et al., "Biomorphic transformation to obtain hierarchical porous structures", 9th IEEE Conference on Nanotechnology, 2009, 609-612.
Ruffini, et al., "Towards Hierarchically Organized Scaffolds for Bone Substitutes from Wood Structures", Key Engineering Materials, vol. 361-363, 2008, 959-962.
Tampieri et al., From wood to bone: multi-step process to convert wood hierarchical structures into biomimetic hydroxyapatite scaffolds for bone tissue engineering, J. Mater. Chem., vol. 19, pp. 4973-4980, 2009.
Orlando, Bruno, et al. "Leader genes in osteogenesis: a theoretical study." Archives of oral biology 58.1 (2013): 42-49.
Gabusi, Elena, et al. "Extracellular calcium chronically induced human osteoblasts effects: specific modulation of osteocalcin and collagen type XV." Journal of cellular physiology 227.8 (2012): 3151-3161.
Ruffini, Andrea, Simone Sprio, and Anna Tampieri. "Study of the hydrothermal transformation of wood-derived calcium carbonate into 3D hierarchically organized hydroxyapatite." Chemical engineering journal 217 (2013): 150-158.

*Primary Examiner* — Shirley V Gembeh
(74) *Attorney, Agent, or Firm* — Meunier Carlin & Curfman LLC

(57) ABSTRACT

The present disclosure relates to a hydroxyapatite obtained from porous wood, having high compressive strength and dimensions suitable for clinical applications. The porous wood has a porosity of between about 60% and about 95%, said porosity being measured after subjecting the wood to a step of pyrolysis, and is selected from among rattan, pine, abachi, balsa, sipo, oak, rosewood, kempas and walnut wood. The hydroxyapatite may be substituted with one or more ions such as magnesium, strontium, silicon, titanium, carbonate, potassium, sodium, silver, gallium, copper, iron, zinc, manganese, europium, gadolinium. Also disclosed is a bone substitute comprising hydroxyapatite obtained from porous wood. The bone substitute is utilized for the substitution and regeneration of a bone or a bone portion, preferably for bones subjected to mechanical loads, such as long bones of the leg and arm, preferably the tibia, fibula, femur, humerus and radius. The invention relates also to a process for manufacturing a biomorphic hydroxyapatite scaffold from wood.

16 Claims, 25 Drawing Sheets

CaCO3 disclosure

CaO + CO2 + H2O = CaCO3 + H2O

LARGE 3D POROUS SCAFFOLDS MADE OF ACTIVE HYDROXYAPATITE OBTAINED BY BIOMORPHIC TRANSFORMATION OF NATURAL STRUCTURES AND PROCESS FOR OBTAINING THEM

CROSS REFERENCE TO RELATED APPLICATIONS

This application is a divisional application of U.S. application Ser. No. 15/750,568 filed Feb. 6, 2018, which is a National Stage application of PCT/IB2016/054665 filed Aug. 3, 2016, which claims priority to Italian Application No. 102015000042834, filed Aug. 6, 2015, and Italian Application No. 102015000042762, filed Aug. 6, 2015, which are hereby incorporated herein by reference in their entirety.

The present disclosure relates to hydroxyapatite obtained from porous wood. In particular, the present disclosure relates to a biomorphic hydroxyapatite scaffold obtained from porous wood for use as a bone substitute. The disclosure relates also to a process to convert wood into a biomorphic hydroxyapatite scaffold which can be used as bone substitute.

BACKGROUND

Current ceramic processing and engineering are based on a well-established sequence of processes enabling the production of large 3D bodies. More specifically, innovative ceramic phases can be synthesized as powders, where specific features such stoichiometry/ion substitutions, nanosize, and surface activity, are responsible for specific functionalities. The ceramic processing currently used to obtain macroscopic 3D ceramic bodies with adequate shape and porosity implies thermal treatment (sintering) of the synthesized ceramic powders suitably formed into a 3-D body (to consolidate the body). All these steps are needed to obtain 3D ceramics with adequate physicochemical and mechanical properties, most of which are degraded during the above-mentioned ceramic process (particularly the sintering treatment). The serious limitations in the development of functional ceramic material, associated with the current ceramic process, impede further progress in the field. Nowadays, with the evolution of modern society, technological products are assuming a steadily increasing role in the life and productivity of people, so that there is a strong need for smart tools able to provide solutions to complex and personalized demands, in various fields of application, e.g. health, environment, energy. Therefore, there is a wide consensus that new approaches are needed for the repeatable and massive production of macroscopic devices with complex structural organization at the macro-scale but, at the same time with a complex structure defined at the nanoscale, and even at the crystal scale. Such macro and nano-structures are relevant to induce non-trivial, but smart functional effects.

With respect to the above-mentioned issues regarding ceramic materials, a paradigmatic change is required in order to develop large highly active ceramics with complex micro and macro-structures.

Bone scaffolds, with particular focus to the regeneration of large, load-bearing bone defects, can be taken as a representative example since they should be porous 3-D ceramics with high bioactivity, in order to be able to be colonized by cells and ultimately regenerated as large bone defects. Indeed, no adequate solutions have been found to date to solve this clinical need.

For many decades, hydroxyapatite ($Ca_{10}(PO_4)_6(OH)_2$) has been recognized as the prime material for bone scaffolding, as it closely resembles the composition of bone mineral and has demonstrated excellent biocompatibility and osteoconductivity. However, the biomimicry of hydroxyapatite is related to its nanosize and the presence of multiple ions, partially replacing calcium and phosphate in the apatite lattice, which are the source of the biological activity of the bone during new tissue formation, remodeling and resorption.

The application of the sintering treatment to hydroxyapatite scaffolds activates surface and bulk reactions at the interface between adjacent hydroxyapatite grains that yield crystal ordering, with expulsion of foreign ions from the apatite lattice, and grain coalescence up to several micrometers, with reduction of specific surface, hydrophilicity and affinity with proteins and cells.

The extensive grain coalescence activated by the sintering process yields consolidation of the whole hydroxyapatite body through reduction of the intergranular porosity and, in turn, of the overall volume. This also generates residual stresses which are among the main sources of structural defects in the ceramic materials. Indeed, the accommodation of residual stresses in ceramic materials is difficult due to their high rigidity (compared to metals and polymers), and is among the most significant factors impairing the mechanical performance of ceramic materials, particularly in the case of large pieces characterized by complex shapes and porous structures, where volume variations following heating/cooling cycles easily provoke critical structural damage.

For the above reasons, the classical ceramic synthesis process does not allow ceramic materials, in particular hydroxyapatites having a biomimetic composition and structure, high bioactivity and resorbability, to be manufactured. This is especially true when large porous 3D ceramics are synthesized for the regeneration of critical size bone defects (i.e. ≥2 cm).

Biomimetic composition and structure are of pivotal relevance for inducing the regenerative cascade in vivo that can uniquely determine and promote regeneration of large, load-bearing bone parts such as the long bones of the limbs. These phenomena, which are closely inter-related and must occur in synergy to activate and sustain the regeneration of bone with all its functions, are: i) fast osteogenesis, osteoconduction and osteointegration; ii) extensive blood vessel formation; iii) ability of progressive bio-resorption.

Fast osteogenesis and osteoconduction enable extensive bone formation and penetration into the scaffold, thus resulting in tight bone/scaffold interface and optimal osteointegration. To achieve these effects, bone-like chemical composition as well as wide open and interconnected porosity are required, so that besides extensive penetration of new bone tissue, a simultaneous formation of a vascular network assisting the formation and maturation of the new bone can be achieved. Incomplete colonization of the scaffold may result in the formation of voids, fibrous tissues or necrotic areas, and will reduce the overall strength and biomechanical performance of the bone/scaffold construct.

Within times compatible with new bone formation, the scaffold should be progressively resorbed, to achieve optimal regeneration of the bone following damage or disease. All the 3D bone scaffolds developed so far are based on sintered calcium phosphates that are crystalline materials hampering osteoclast activity, compared to nanocrystalline, nanosized, ion-substituted apatite; therefore, even though porous bone hydroxyapatite scaffolds can be well integrated into the surrounding bone by surface adhesion, the lack of bio-resorption does not allow the complete remodeling process, i.e. replacement of the scaffold with the new bone. This results in incomplete recovery of the functional ability of the diseased bone, particularly in the case of very long, load-bearing, bone segments.

Particularly in the case of long, load-bearing bones, the scaffold must also exhibit adequate mechanical performance, while maintaining wide open macro-porosity, which is a challenge considering that these features are normally inversely related (i.e. the higher the porosity, the lower the mechanical resistance) and that a high porosity extent is required to provide adequate scaffold colonization and osteointegration. This is one of the most relevant factors limiting the application of current scaffolds in the regeneration of extensive portions of long, load-bearing bones. In this respect, scaffolds with hierarchically-organized porous structures can exhibit superior mechanical performance compared to materials with similar, but randomly organized porosity. In this respect, only scaffolds with such an organized structure can efficiently activate mechano-transduction processes at the cell level, thus triggering regeneration of mature, organized and mechanically-competent bone.

The proposed innovation is based on a paradigmatic change from the classical ceramic synthesis process to a new fashion of reactive sintering that enables the generation of ceramic phases with defined chemical composition, organized into a large 3D body with complex morphology, hierarchical structure and, at the same time, optimized mechanical performance, starting from hierarchically organized natural structures. In this respect biomorphic transformation is the fulcrum of this innovative approach that can be applied to hierarchically organized natural structures (e.g. woods, plants, exoskeletons).

Biomorphic transformation of ligneous structures to bone-mimicking ceramics was successfully attempted using woods with porous structures such as pinewood and rattan, and denser woods such as red oak and sipo, as templates for reproducing the structure and mechanical performance of spongy and cortical bone, respectively.

The use of wood in the formation of biomimetic hydroxyapatite scaffolds was reported by Anna Tampieri et al. in the *Journal of Material Chemistry*, 2009, 19, 4973-4980. In this publication, Tampieri et al. describe the process of converting 1 cm long pieces (therefore a small piece, not adequate for regeneration of critical size defects) of rattan wood and pine wood into hydroxyapatite. The process involved pyrolysis of the wood specimens at a temperature of 1000° C. using a slow heating rate, followed by carburization wherein the carbon template was transformed into calcium carbide. Carburization was achieved by either liquid phase infiltration or vapour phase infiltration. Vapour infiltration was performed at temperatures higher than the boiling point of calcium (1484° C.). The carburization process involved initial heating the pyrolised wood to 800° C., followed by heating to 1100° C. and finally to 1650° C. for 3 hours. It was necessary to heat the pyrolised wood to this temperature for 3 hours to ensure that the reaction went to completion. Following carburization, the three dimensional calcium carbide scaffold was oxidized to transform the calcium carbide to calcium oxide, while preserving the morphology of the native wood. After oxidation, the three dimensional calcium oxide scaffold was carbonated to transform the calcium oxide scaffold into calcium carbonate scaffold. High pressure values (2.2 MPa) were employed to allow the penetration of $CO_2$ across the forming $CaCO_3$ scale, up to the core of the CaO structure. Finally, a phosphatization step was carried out to transform the calcium carbonate scaffold into hydroxyapatite scaffold with hierarchically organized anisotropic morphology resembling that of the native wood. During this step, the wood-derived $CaCO_3$ templates were soaked in an aqueous solution of $KH_2PO_4$ at a temperature of 200° C., under a pressure of 1.2 MPa for 24 hours.

The process described above yielded hydroxyapatite ceramic scaffolds with the hierarchically organized anisotropic morphology of native wood.

The compressive strength of the scaffold derived from pinewood, measured in the longitudinal direction ranged between 2.5 and 4 MPa, and in the transversal direction, ranged between 0.5 and 1 MPa. Therefore only scaffolds of limited dimension, typically of less than 1 cm, are obtainable by said process. The low values of compression strength, also in association with a size s 1 cm, make these scaffolds not relevant for bone regeneration, particularly in the case of load-bearing bones. In fact, it is accepted that, to be critical, a bone defect should have a length of 2-3 times the diameter of the affected bone. Hence, scaffold of 1 cm in size cannot be considered as useful in this respect.

The phosphatization step mentioned above in the conversion of wood to hydroxyapatite, was reported in more detail by Ruffini et al. in Chemical Engineering Journal 217 (2013) 150-158. In this publication, cylindrical templates of rattan-derived calcium carbonate having diameters of 8 mm and lengths of 10 mm were used as starting materials. The phosphatization process was carried out using aqueous solutions of diammonium hydrogen phosphate, ammonium dihydrogen phosphate and ammonia.

Patent application WO 2012/063201 published on 18 May 2012, describes a bone substitute comprising a core, based on hydroxyapatite, obtained from at least one porous wood, and a shell based on hydroxyapatite or silicon carbide obtained from at least one wood having a lower porosity than the at least one wood of the core. The shell was prepared in a hollow cylindrical shape suitable for accommodating the core, which could be prepared as a solid cylinder that is inserted into the cavity of the shell. The process for obtaining the bone substitute from wood is also described in the application. The first step is pyrolysis of a native wood such as rattan or pine, by heating it to a temperature of between 800 and 2000° C. From this process, a carbon material is obtained. In the second step, the carbon material is transformed into calcium carbide at a temperature of between 1500 to 1700° C. Next, the calcium carbide is oxidized at a temperature between 900 and 1000° C. In order to convert the calcium oxide material to calcium carbonate, carbonation is performed in an autoclave at a temperature of 400° C. with a $CO_2$ pressure of 2.2 MPa for 24 hours. The calcium carbonate material is then transformed into hydroxyapatite partially substituted with carbonate by phosphatization. The resulting hydroxyapatite scaffolds derived from rattan, have a compressive strength of between 4 and 5 MPa in the longitudinal direction, and a compressive strength of 1 MPa in the transversal direction.

Although the publications mentioned above describe the successful transformation of wood such as rattan and pine into hydroxyapatite, while fairly reproducing the three-dimensional morphology of the wood, scaffolds exhibiting features adequate for regeneration of long segments of load-bearing bone could not be obtained.

Indeed all of the mentioned publications refer to hydroxyapatite scaffolds obtained from wood, having small dimensions (i.e. a volume of less than 1 $cm^3$) that cannot have real clinical applications, particularly for the regeneration of large, load-bearing bone parts. The processes described in the prior art are not suitable for manufacturing hydroxyapatite scaffolds having dimensions that are convenient for clinical applications, such as for the regeneration of critical size load-bearing bone defects where large scaffolds, i.e. with size at least equal to 2 cm, are needed.

Thus there remains a need in the art for a biomorphic scaffold, in particular a porous 3D scaffold, with a biomimetic chemical composition that exhibits adequate mechanical performance, a morphology that is favorable to cell colonization and vascular growth and, at the same time, which has dimensions that are suitable for clinical applications.

Such a biomorphic scaffold would be particularly suitable for bone regeneration, in particular for implantation in load-bearing bone defects, such as long bones of the limbs (e.g. femur, tibia, humerus, fibula, radius), but also for the substitution and regeneration of spine bones (e.g. vertebral bodies, intervertebral disc), cranial bone-parts or maxillofacial bone-parts.

The present disclosure meets the above needs by providing a biomorphic scaffold, preferably a hydroxyapatite scaffold particularly suitable for bone substitution and regeneration, in particular for substitution and regeneration of long load-bearing bones.

The present disclosure meets the above needs also by providing a process for the manufacturing of a biomorphic scaffold, preferably a 3D biomorphic scaffold. In particular, the biomorphic scaffold is a hydroxyapatite scaffold.

SUMMARY OF THE DISCLOSURE

In general, the present disclosure describes a hydroxyapatite scaffold obtained from a wood having a total porosity of between 60% and 95%, said porosity being measured after subjecting the wood to a step of pyrolysis, the scaffold having a length, measured along a direction in which a dimension of the scaffold is maximum, greater than or equal to 2 cm.

More particularly the present disclosure describes a biomorphic hydroxyapatite scaffold obtained from a wood having a total porosity of between 60% and 95% (said porosity being measured after subjecting the wood to a step of pyrolysis), said hydroxyapatite being characterized by a hierarchically organized pore structure and a compressive strength of greater than 5 MPa, preferably between 10 MPa and 20 MPa, measured in the direction along the channel-like pores (longitudinal direction).

Preferably the hydroxyapatite of the disclosure shows a compressive strength along the perpendicular direction of the long axis of the channels (transversal direction) of up to 10 MPa.

Preferably, the biomorphic hydroxyapatite scaffold obtained from wood, has a hierarchically organized pore structure that derives from the hierarchically organized pore structure of the wood from which it is obtained (native wood).

The present disclosure also refers to a biomorphic hydroxyapatite scaffold derived from wood, wherein the hydroxyapatite is partially substituted (doped) with one or more ions selected from the group comprising magnesium, strontium, silicon, titanium, carbonate, sodium, potassium, gallium, silver, copper, iron, zinc, manganese, europium and gadolinium.

The wood from which the biomorphic hydroxyapatite is derived has a total porosity of between 60% and 95%, preferably between 65% and 85% (said porosity being measured after subjecting the wood to a step of pyrolysis). Woods exhibiting porosity within these ranges include rattan, pine, abachi, balsa, sipo, oak, rosewood, kempas and walnut wood. Preferably the biomorphic hydroxyapatite is obtained from rattan wood.

The biomorphic hydroxyapatite scaffold obtained from wood of the disclosure has structural cohesion and mechanical properties which render it particularly suitable for use as a bone substitute.

Therefore, the present disclosure refers to the use of the biomorphic hydroxyapatite scaffold as bone substitute, as well as to a bone substitute comprising said biomorphic hydroxyapatite scaffold. The disclosure refers also to a bone substitute consisting of said biomorphic hydroxyapatite scaffold.

The biomorphic hydroxyapatite scaffold derived from wood may be used as a bone substitute for regenerating a bone or a bone portion, in particular human and animal bones. Preferably, the biomorphic hydroxyapatite scaffold derived from wood may be used as a bone substitute for bones or bone portions which are subjected to mechanical loads. More preferably the bone or bone portions are long bones of the leg and arm such as the tibia, fibula, femur, humerus and radius.

The biomorphic hydroxyapatite scaffold derived from wood may also be used in the substitution and/or reconstruction of cranial bone-parts, maxillofacial bone-parts and spine bones (e.g. vertebral bodies, intervertebral disc).

The biomorphic hydroxyapatite scaffold of the disclosure can also be used as a filter for liquids or gases.

The present disclosure also describes a process for obtaining a biomorphic hydroxyapatite scaffold derived from wood.

More particularly the present disclosure describes a process for producing a biomorphic hydroxyapatite scaffold having a length, measured along a direction in which a dimension of the scaffold is maximum, greater than or equal to 2 cm, which comprises the steps of pyrolysis, carburization, oxidation, hydration, carbonation and phosphatization of a piece of wood (native wood) having a total porosity of at least 20%, preferably at least 40%, more preferably comprised between 60% and 95%, wherein said porosity is measured after subjecting the wood to the step of pyrolysis. Examples of native wood that can be subjected to the process of the invention are: rattan, pine, abachi, balsa, sipo, oak, rosewood, kempas and walnut.

While multiple embodiments are disclosed, still other embodiments will become apparent to those skilled in the art from the following detailed description. As will be apparent, certain embodiments, as disclosed herein, are capable of modifications in various obvious aspects, all without departing from the disclosure. Accordingly, the drawings and detailed description are to be regarded as illustrative in nature and not restrictive.

BRIEF DESCRIPTION OF THE FIGURES

The following figures illustrate preferred embodiments of the subject matter disclosed herein. The claimed subject matter may be understood by reference to the following description taken in conjunction with the accompanying figures, in which:

FIG. 13—bottom two pictures show a comparison of the dimension of the carcium carbide granes;

DETAILED DESCRIPTION OF THE DISCLOSURE

Figure 1:
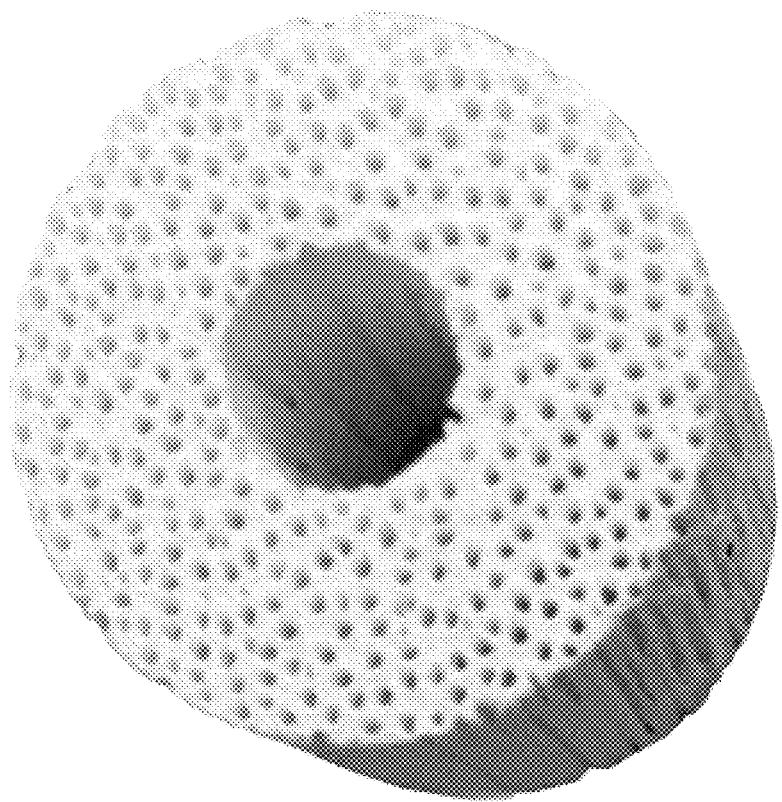
FIG. 1 shows a particular embodiment of the biomorphic scaffold that features a central channel.
Figure 2:
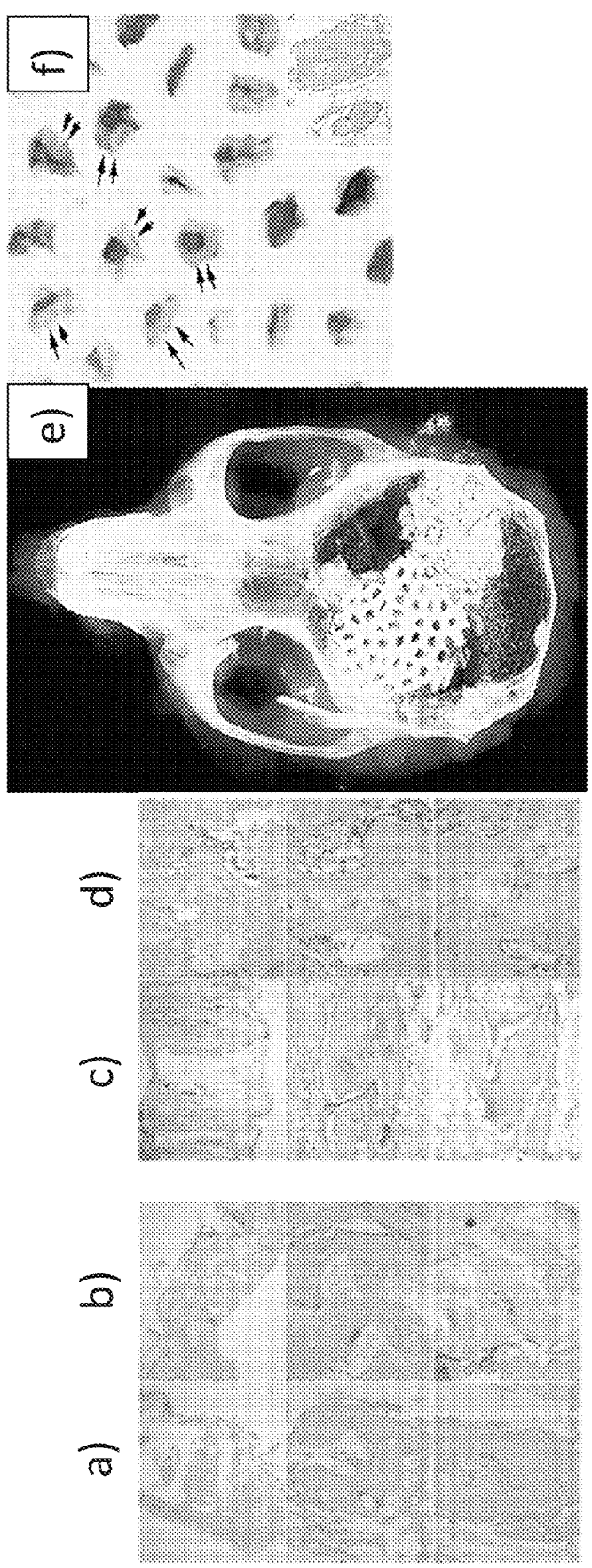
FIG. 2 shows photographs depicting tissues of explanted mice calvaria after 8 weeks. Extensive bone formation and penetration of the scaffold pores was achieved to a similar extent when implanted alone or with osteogenic stromal cells, where a) represents wood and no cells, b) represents hydroxyapatite and no cells, c) represents wood and cells, d) represents hydroxyapatite and cells, and where e) represents the scaffold implanted in a critical size defect of a mouse calvaria. The arrows in FIG. 2 f) point to the channel-like pores of the scaffold shown in FIG. 2 e) which mimic Haversian systems. Haversian systems or osteons are the functional unit of compact bone, in the form of cylinders made of bone lamellae organized in concentric layers. In the middle of the osteons a channel exist, containing the bone's nerve and the blood supply.

As used in present description and in the appended claims, "hierarchical pore structure" or "hierarchically organized pore structure" indicates a material having an anisotropic three dimensional pore structure in which channel-like pores are interconnected through transversal channels and wherein micro and nano-pores are present in the area surrounding the channel-like pores.

As used in the present description and the appended claims, the values of "compressive strength" are obtained with the method described in the following description by exerting mechanical forces along the longitudinal and transversal directions, with respect to the channel-like pores.

As used in the present description and the appended claims, "bone defect" refers to a missing part or portion of the bone or to the entire bone that is missing and needs to be totally replaced by the scaffold of the disclosure.

As used in the present description, "biomorphic hydroxyapatite" refers to a material that: 1) consists of hydroxyapatite or 2) comprises hydroxyapatite or 3) is a material comprising or consisting of hydroxyapatite and tricalcium phosphate. In case the material consists of hydroxyapatite and tricalcium phosphate, the material is a biphasic material. In an embodiment of the invention, when the "biomorphic hydroxyapatite" is a material comprising or consisting of hydroxyapatite and tricalcium phosphate, the hydroxyapatite is doped with one or more ions chosen in the group consisting of magnesium, strontium, silicon, titanium, carbonate, potassium, sodium, silver, gallium, copper, iron, zinc, manganese, europium, gadolinium and mixtures thereof.

The inventors of the present patent application have surprisingly found that it is possible to obtain a biomorphic hydroxyapatite scaffold from wood which exhibits a biomimetic chemical composition, an adequate mechanical performance, a morphology that is favorable to cell colonization and vascular growth and, at the same time, has dimensions that are suitable for clinical applications.

In a first aspect, the present disclosure describes a biomorphic hydroxyapatite scaffold obtained from a wood having a total porosity of at least 20%, preferably at least 40%, more preferably comprised between 60% and 95%, wherein said porosity is measured after subjecting the wood to the step of pyrolysis, the scaffold having a length, measured along a direction in which a dimension of the scaffold is maximum, greater than or equal to 2 cm.

The total porosity of the biomorphic hydroxyapatite scaffold obtained after the process of the disclosure is the same as the total porosity of the starting wood measured after subjecting the wood to the step of pyrolysis. In particular, the total porosity of the biomorphic hydroxyapatite scaffold obtained after the process of the disclosure is at least 20%, preferably at least 40%, more preferably comprised between 60% and 95%.

Preferably, the scaffold has a length, measured along a direction in which a dimension of the scaffold is maximum, that is greater than or equal to 2 cm and reaches an end value that is determined according to the clinical application. For example in the case of bone substitution of long bones, such as tibia, femur, fibula, humerus, radius, the length of the scaffold, measured along a direction in which a dimension of the scaffold is maximum, can be comprised between 2 and 20 cm.

Preferably, the scaffold of the disclosure has a compressive strength measured in the longitudinal direction of greater than 5 MPa, preferably between 10 MPa and 20 MPa.

Preferably the scaffold of the disclosure shows a compressive strength along the transversal direction of up to 10 MPa.

Preferably, the biomorphic hydroxyapatite scaffold is characterized by a hierarchically organized pore structure.

The "hierarchical pore structure" or "hierarchically organized pore structure" of the hydroxyapatite scaffold of the disclosure derives from the complex three-dimensional hierarchical structure of the starting wood from which the scaffold is obtained and therefore has a range of differently sized pores. The differently sized pores in the hierarchical structure render it desirable for use as a bone substitute.

For example, pores having diameter≥200 μm, preferably between 150-300 μm, more preferably 200-300 μm will permit cell colonization and proliferation and the formation of an appropriate vascularization tree. Pores having a diameter s 10 μm, preferably <1 μm, more preferably between 0.01 and 0.1 μm (micro and nano-pores), that partially interconnect the channel-like pores, permit exchange of nutrient fluids and discharge of the waste products of cell metabolism.

The preservation of the hierarchical pore structure of wood in the hydroxyapatite, provides scaffolds with optimal mechanical features and enables the efficient discharge of mechanical loads.

As hydroxyapatite obtained from wood reproduces the structure of a natural material in detail, it can be thus referred to as being biomorphic.

In particular, the hierarchically organized pore structure of the scaffold of the disclosure includes between 30% and 80% (of the total porosity) of pores having a diameter below 150 μm, the reminder to 100% of total porosity being pores having diameter greater than 150 μm.

In one embodiment, preferably when the starting wood is rattan, between 30% and 60% of the total porosity of the scaffold is due to pores having a diameter≤10 μm.

In one embodiment, preferably when the starting wood is rattan, at least 25% of the total porosity, preferably between 25% and 50% of the total porosity of the hydroxyapatite scaffold is due to pores having a diameter≤1 μm, preferably ≤0.1 μm, in particular between 0.01 and 0.1 μm.

In one embodiment, preferably when the starting wood is rattan, at least 20% of the total porosity of the hydroxyapatite scaffold is due to pores that have diameter≥150 μm.

Preferably, the hydroxyapatite scaffold has a specific surface area (SSA)>9 m$^2$/g, preferably from 9 to 20 m$^2$/g.

The wood used to obtain the hydroxyapatite scaffold can be any wood having a total porosity of at least 20%, preferably at least 40%, more preferably comprised between 60% and 95%, even more preferably a porosity of between 65% and 85% (said porosity being measured after subjecting the wood to a step of pyrolysis).

Examples of suitable woods used to obtain the hydroxyapatite include rattan, pine, abachi, balsa, sipo, oak, rosewood, kempas and walnut wood, preferably the wood used is rattan wood.

The hydroxyapatite scaffold obtained from wood may comprise hydroxyapatite which is partially substituted with one or more ions. Examples of such ions are carbonate, magnesium, strontium, silicon, titanium, sodium, potassium, silver, gallium, copper, iron, zinc, manganese, europium and gadolinium. The introduction of carbonate in the phosphate site increases bio-solubility and enhances surface affinity to osteoblast cells.

The introduction of magnesium provides enhanced ability of new bone apposition and formation. The introduction of strontium assists in re-establishing bone production, affected by metabolic diseases such as osteoporosis, so that its presence may enhance bone regeneration.

The introduction of silver, gallium, copper and zinc provides antibacterial properties. When the hydroxyapatite scaffold obtained from wood comprises hydroxyapatite which is partially substituted with one or more ions, the scaffold is a material comprising or consisting of doped hydroxyapatite and tricalcium phosphate. According to a further embodiment, the biomorphic hydroxyapatite scaffold of the instant disclosure may comprise:

0-15 wt % of magnesium, preferably 1-10 wt %; and/or
0-15 wt % of carbonate, preferably 1-10 wt %; and/or
0-15 wt % of strontium, preferably 1-10 wt %; and/or
0-20 wt % of titanium, preferably 1-10 wt %; and/or
0-15 wt % of potassium, preferably 1-10 wt %; and/or
0-15 wt % of sodium, preferably 1-10 wt %; and/or
0-15 wt % of silicon, preferably 1-10 wt % and/or;

0-15 wt % of silver, preferably 1-10 wt % and/or;
0-15 wt % of gallium, preferably 1-10 wt % and/or;
0-15 wt % of copper, preferably 1-10 wt % and/or;
0-30 wt % of iron, preferably 1-10 wt %; and/or
0-15 wt % of zinc, preferably 1-10 wt % and/or;
0-15 wt % of manganese, preferably 1-10 wt % and/or;
0-15 wt % of europium, preferably 1-10 wt % and/or;
0-15 wt % of gadolinium, preferably 1-10 wt % and/or.

The biomorphic hydroxyapatite scaffold obtained from wood according to the present disclosure, has bioactivity and bioresorbability characteristics combined with mechanical strength characteristics and dimensions that makes it particularly suited for clinical use as a bone substitute, in particular in humans and animals. Such a bone substitute could be used to substitute and/or reconstruct and/or regenerate bone, bone portions or bone defects. For example, the bone substitute could be used to substitute or regenerate bone or bone portions that are subjected to mechanical loads. For example, the bone substitute could be used to substitute or regenerate long bones of the arms and legs. Such long bones could include the tibia, femur, fibula, humerus, radius, etc.

The bone substitute could also be used in the substitution and/or reconstruction of cranial bone-parts, maxillofacial bone-parts and spine bones e.g. vertebral bodies, interverbral disc) and in spinal fusion surgery procedures.

When used as a bone substitute, the biomorphic hydroxyapatite scaffold can have a shape that adapts to the shape of the bone defect that needs to be reconstructed in such a way as to substantially fill the bone gap. Therefore, the scaffold and the bone substitute of the disclosure can have any shape that is suitable for the purpose of reconstructing and regenerating a bone defects or for substituting any missing part of the bone.

For example the scaffold or the bone substitute of the present disclosure may take the form of a cylinder, right prism, or cuboid, or wedges. In one embodiment, the scaffold or the bone substitute comprises a central channel with a diameter of between about 20% to about 60% of the diameter of the scaffold or the bone substitute. In particular, the scaffold or the bone substitute has a tubular shape.

In one embodiment, the present disclosure further refers to a scaffold or a bone substitute having a cylindrical, right prism, cuboid or tubular shape, having a height greater than or equal to 2 cm.

In an embodiment of the present disclosure, the scaffold or the bone substitute may be coated with a thin layer based on hydroxyapatite and/or collagen to increase cellular adhesion and proliferation, and thus osteointegration in the surrounding bone tissue. The layer may additionally comprise hydroxyapatite substituted with one or more ions relevant for the stimulation of the bone regeneration such as carbonate, magnesium, silicon, potassium, sodium and strontium, or with antibacterial effect such as gallium, silver, copper or zinc.

In a further embodiment of the present disclosure, the scaffold or the bone substitute may be soaked in a natural polymer (chosen among the group comprising gelatin, collagen, alginate, chitosan, gellan, cellulose) to further increase mechanical properties and further promoting cell adhesion.

To the scaffold or bone substitute cells, platelet rich plasma, antibodies, growth factors proteins, DNA fragments, miRNA, siRNa can be added in order to help cell adhesion.

Also drugs, such as antibiotics or anticancer drugs, can be added to the scaffold or bone substitute.

The disclosure refers also to a method of reconstruction and/or regeneration of a human or animal bone having a bone defect, comprising the steps of:
  providing a bone substitute comprising or consisting of the biomorphic hydroxyapatite scaffold of the disclosure having a shape that corresponds to the shape of a bone defect;
  implanting the bone substitute in the bone defect of the patient.

Preferably, the method of reconstruction and/or regeneration includes the steps of providing a 3D model of the bone defect and, based on the 3D model obtained, imparting to the scaffold a shape corresponding to the shape of the bone defect. The step of imparting a shape to the scaffold can be applied to the starting piece of wood or to the hydroxyapatite scaffold obtained at the end of the transformation process of the disclosure or to the scaffold obtained after each step of the process (e.g. after the carbonation step). Preferably the step of imparting the shape is applied on the starting piece of wood.

The biomorphic hydroxyapatite scaffold of the disclosure and the biomorphic hydroxyapatite scaffold partially substituted with one or more ions, is obtained from a multistep transformation process comprising the following steps:

1) Pyrolysis: a native wood is heated at a temperature in the range of 600° C. to 1000° C. under an inert atmosphere to permit the decomposition and the elimination of all organic substances. From this process, a carbon template is obtained.

2) Carburization: the carbon template is infiltrated with calcium in the vapour state at a temperature in the range 900 to 1200° C., and at a pressure<1000 mbar, preferably <600 mbar, more preferably in the range of 0.05 to 100 mbar, thus transforming the carbon template into calcium carbide ($CaC_2$).

3) Oxidation: the calcium carbide template is heated in air at a temperature in the range of 750 to 1300° C., preferably 1000-1200° C., thus enabling the transformation of calcium carbide into calcium oxide (CaO).

4) Hydration: the calcium oxide template is exposed to water, thus enabling water uptake in an amount of 1-25 mole %, preferably 5-15 wt %.

5) Carbonation: the calcium oxide template is transformed into calcium carbonate by heating at a temperature in the range of 500 to 900° C., preferably at a temperature in the range of 750 to 850° C. under a $CO_2$ pressure, or a mixture of $CO_2$ and an inert gas (e.g. argon, nitrogen) pressure. The pressure range is from 4 to 20 MPa.

6) Phosphatization: the calcium carbonate template is treated with at least one phosphate salt.

In the pyrolysis step 1) of the multi-step process, the native wood is preferably selected among rattan, pine, abachi, balsa sipo, oak, rosewood, kempas and walnut wood. More preferably the native wood is rattan wood.

The native wood has a total porosity of at least 20%, preferably at least 40%, more preferably comprised between 60% and 95%, wherein said porosity is measured alter subjecting the wood to the step of pyrolysis.

Prior to the pyrolysis step 1), the starting native wood may be optionally dried at a temperature of between 50° C. and 90° C., preferably at a temperature of between 60° C. and 80° C., more preferably at a temperature of between 65° C. and 75° C. The native wood may be dried for more than 6 hours, preferably for more than 12 hours, preferably for more than 18 hours, preferably for a time comprised between 20 and 30 hours.

In the pyrolysis step of the multi-step process, the inert atmosphere may be an atmosphere of a gas selected from the group comprising nitrogen and argon.

In the pyrolysis step of the multi-step process, the native wood may be heated at a temperature of between 600° C. to 1000° C., preferably at a temperature of between 800° C. and 1000° C. The pyrolysis step may last more than 6 hours, preferably more than 12 hours, preferably more than 18 hours, preferably said step may last for a time comprised between 20 and 30 hours.

The thermal cycle of the pyrolysis step 1) may be carried out by heating the native wood at the rate not higher than 5° C./min, preferably not higher than 3° C./min and by cooling at a rate not higher than 3° C./min, preferably not higher than 2° C./min, to prevent crack formation and internal fracture of the material.

Prior to the pyrolysis step 1), the multistep method can additionally comprise a step i) of selection and preparation of the native wood, wherein said native wood can be cut into a piece having a shape corresponding to the shape of a bone defect to be reconstructed. In particular the native wood is shaped into a piece of wood having a length, measured along a direction in which a dimension of the wood is maximum, that is greater than or equal to 2 cm. Preferably, the dimension of the wood reaches an end value that is determined according to the clinical application.

For example, the native wood can be shaped in the form of a cylinder, right prism, or cuboid. The native wood can also be shaped in such a way as to comprise a central channel with a diameter of between about 20% to about 60% of the diameter of the piece of wood. In particular, the native wood can be cut into a tubular shape.

Preferably, step i) of selection and preparation of the native wood, comprises the steps of: providing a 3D model of a bone defect and, based on the 3D model obtained, imparting to the native wood a shape corresponding to the shape of the bone defect. The step of imparting a shape to the native wood can be applied to the starting native wood or to the hydroxyapatite scaffold obtained at the end of the multi-step transformation process. Preferably the step of imparting the shape is applied on the starting native wood to avoid internal and external damage (fracture) of the scaffold.

In the carburization step 2) of the multi-step process, the reaction is preferably carried out with a Ca/C molar ratio (at the beginning of the reaction) in the range of 1.10 to 2.50, preferably in the range of 1.50 to 2.00. The Ca/C molar ratio is important because ratios below the range lead to incomplete reactions and ratios above the range lead to obstruction of the pores by residues of Ca.

In the carburization step of the multi-step process, the carbon template is heated at a heating rate in the range of 1 to 10° C./min, preferably at a heating rate in the range of 1 to 7° C./min.

The inventors of the present patent application have surprisingly found that carrying out the carburization step at a reduced pressure as above described is an advantage for the successful application of the subsequent process steps, particularly when large biomorphic scaffold needs to be produced.

In fact, by using the above-described pressure conditions, the evaporation of calcium can occur at temperatures that are about 400-500° C. lower than the boiling point of calcium at room atmosphere (i.e. 1484° C.), thus yielding, unexpectedly, the complete transformation of the pyrolized wood into calcium carbide at a temperature much lower than any other process known in the art. In particular, the use of pressure in the range of 0.5-600 mbar, or preferably 0.05 to 100 mbar, results in a substantially complete transformation of the pyrolized wood into calcium carbide.

A substantially complete transformation of the pyrolized wood into calcium carbide will result in an advantage for the yields of the subsequent transformation steps.

The carburization conditions of the present disclosure also improve preservation of the micro- and nano-pores having diameters≤1 μm (preferably from 0.01 to 0.1 μm) of the native wood both in the scaffold after carburization and in the final biomorphic scaffold, with respect to the known scaffolds obtained from wood using known processes.

The carburization phase is a critical step in the process because a good preservation of the micro- and nano-porosity after this step will ensure that the final biomorphic scaffold exhibits similar nano/micro-porosity. The presence of a high percentage of well interconnected micro and nano-pores in the final biomorphic scaffold permits exchange of nutrient fluids and discharge of the waste products of cell metabolism.

Besides improving the preservation of the micro- and nano-pores having diameters≤1 μm, the carbonization conditions here described yield a scaffold after carburization (and also a final biomorphic scaffold) with specific surface area (SSA) from 9 to 20 $m^2/g$. Such a specific surface area is about 2-fold higher than the SSA of a scaffold obtained with a process known in the art—which is about 5-6 $m^2/g$ (see comparative example 4 and FIGS. 10-13).

Figure 13:
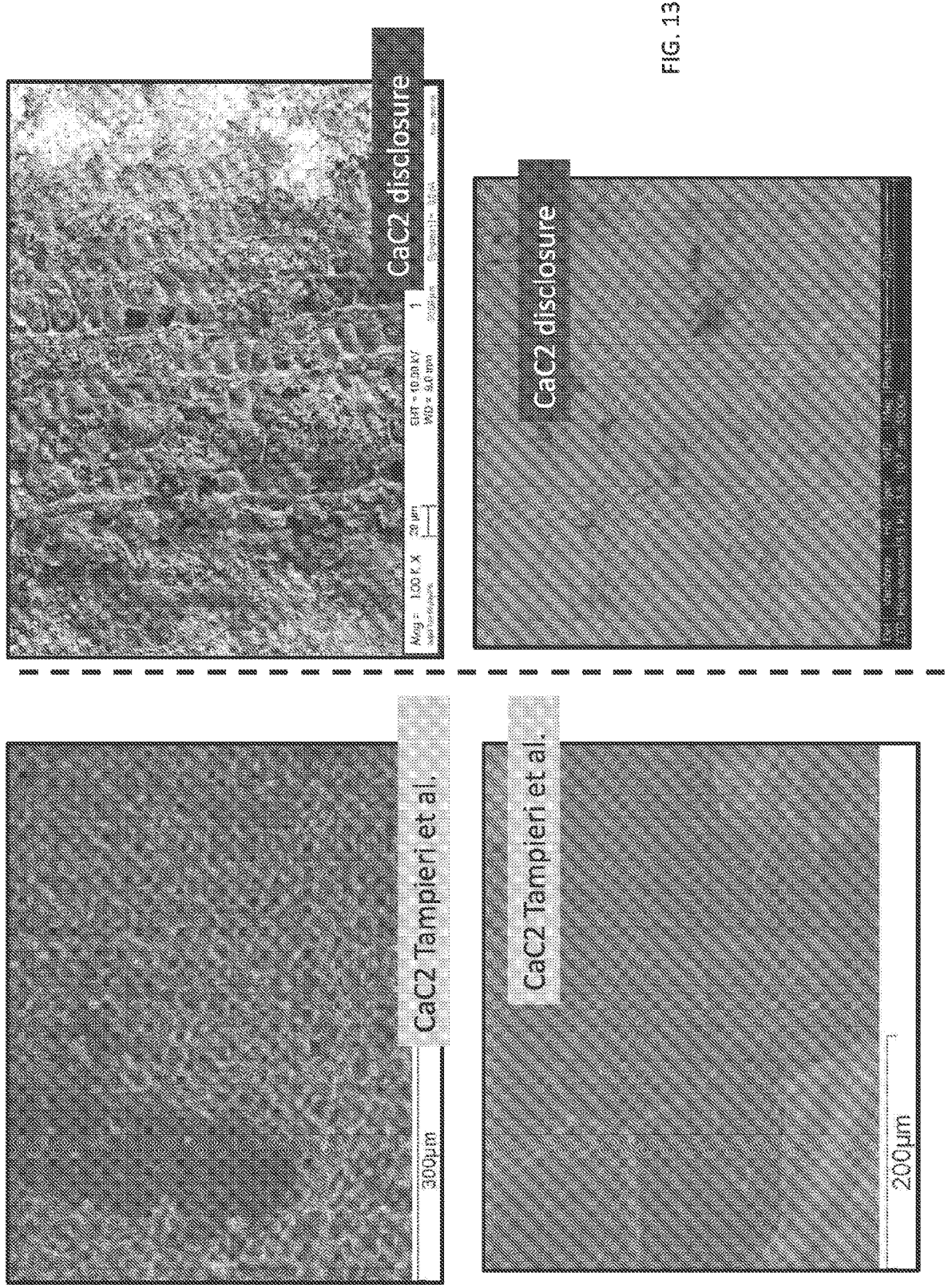

The carburization conditions of the present disclosure also yield a porous calcium carbide scaffold containing calcium carbide grains that are smaller than the grains of a scaffold obtained with a known process (see comparative example 4 and FIG. 13—bottom pictures).

The comparative examples show that the dimensions of the calcium carbide grains in the scaffold after carburization according to the present disclosure is about 5-15 μm (preferably about 10 μm), while the crystal dimensions of the scaffold after carburization obtained with known processes is about 100 μm.

The inventors of the present patent application have surprisingly found that the higher specific surface area (SSA) and the smaller dimension of the grains that are obtained with the carburization conditions above-described, and could not obtained by previously disclosed methods, is important to ensure high yield of transformation of the native wood after each step of the process.

Figure 14:
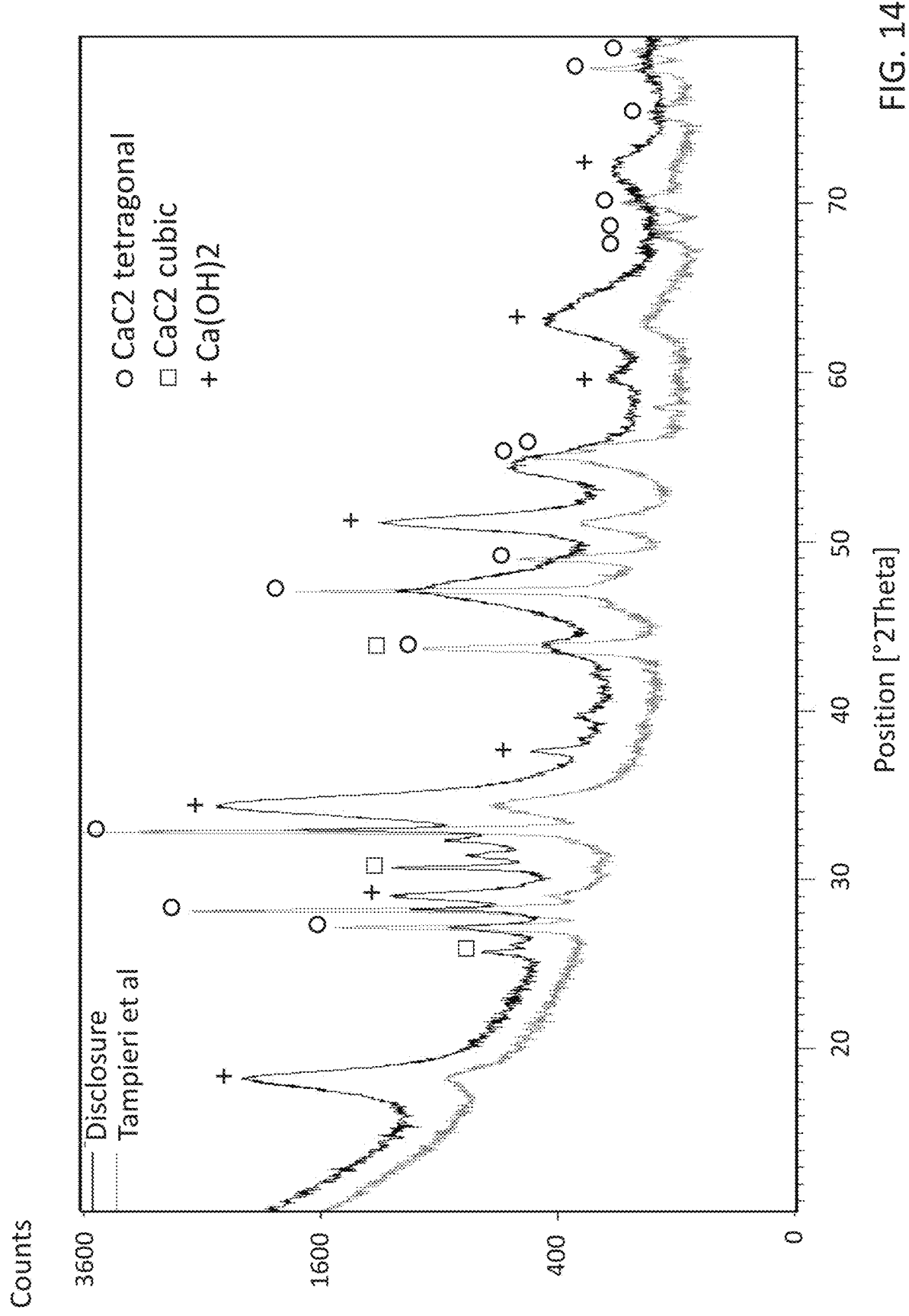
FIG. 14 show a comparison of the crystal phase of the two calcium carbide scaffolds, measured with x ray-XRD, obtained with the process of the invention and the prior art process, respectively.

Comparative example 4 and FIG. 14 also show that the scaffold after carburization according to the present disclosure contains calcium carbide with a mixture of tetragonal and cubic crystal lattice, while the scaffold obtained with known processes contains calcium carbide with a tetragonal crystal lattice only. Since calcium oxide has a cubic crystal structure only, the transformation from a calcium carbide, which is partially in a cubic form, to calcium oxide, can occur with a lower risk of generating microfractures in the scaffold. This is extremely advantageous for the quality of the final biomorphic scaffold.

Therefore, the conditions employed in the carburization step strongly reduce the number of defects that can be observed in the hierarchical pore structure of the calcium carbide.

In addition, the low temperatures employed in the present disclosure (i.e. well below 1500° C.) prevent grain coalescence and excessive consolidation of the calcium carbide, which provoke structural distortion and deviations from the original microstructure of the starting wood, thus impairing the outcome of the following process steps.

In the oxidation step 3) of the multi-step process, the calcium carbide template may be heated to a final temperature in the range of 800 to 1300° C., preferably to a final temperature in the range of 1000 to 1200° C.

In the oxidation step, the calcium carbide template may be heated at a heating rate in the range of 1 to 15=C/min, preferably at a heating rate in the range of 1 to 7° C./min. The oxidation of calcium carbide obtained under pressure according to the carburization step described above leads to a scaffold of calcium oxide with higher specific surface area (SSA) and a porosity with a higher micro- and nano-pores fraction with respect to scaffolds obtainable with the known processes (see comparative example 4 and FIG. 16). The comparative experiment show that the micro and nano-porosity is conserved also after the oxidation step.

In the hydration step 4) of the multi-step process the calcium oxide template is exposed to water, thus enabling water uptake in an amount preferably comprised in the range of 1-25 mole %, more preferably comprised in the range 5-15 mole %. This step leads to the formation of hydrated calcium oxide containing calcium hydroxide in amount≤50% by weight of the 3D structure, that catalyzes the subsequent carbonation of CaO. The amount of calcium hydroxide $(Ca(OH)_2)$ as intermediate product must be strictly controlled to avoid the collapse of the 3D structure. The hydration conditions here described allow to keep the amount of calcium hydroxide s 50%.

In a preferred embodiment, the hydration step is conducted at the same time as the carbonation step, for example by using $CO_2$ enriched with water.

In the carbonation step 5) of the multi-step process, the use of high temperature while progressively increasing the $CO_2$ pressure in the system up to the values indicated above, surprisingly enables substantially complete conversion of hydrated calcium oxide into a calcium carbonate template which exhibits surprisingly high cohesion and mechanical strength.

The carbonation step of the multi-step process may be carried out according to one of the following thermal cycles:
  at a constant $CO_2$ pressure of about 10-15 MPa, slowly increasing the temperature at a value in the range of about 750-850° C., preferably at about 800° C.;
  at a constant temperature of about 750-850° C. (or about 700-800° C.), preferably at about 800° C. raising the pressure up to about 10-15 MPa;
  keeping the pressure at about 4-6 MPa while raising the temperature up to about 750-850° C. (or about 700-800° C.), preferably up to about 800° C. and subsequently increasing the pressure up to about 10-15 MPa.

Figure 17:
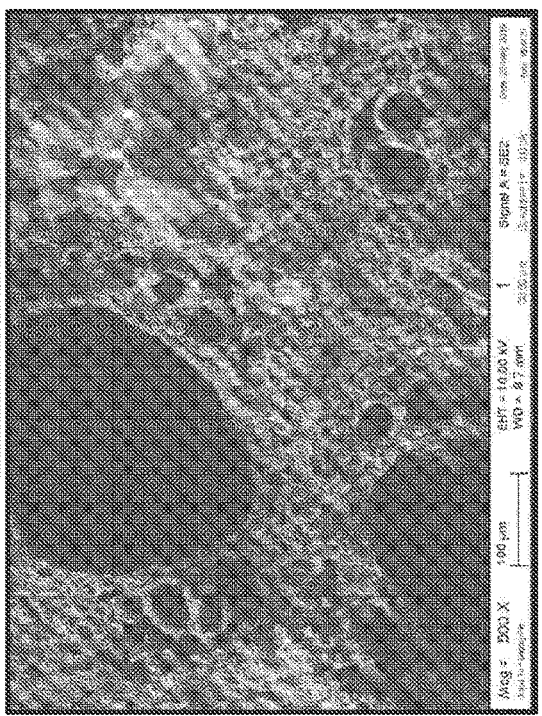
FIGS. 17 and 18 show SEM images of the calcium carbonate obtained after the carbonation step according to the present invention and the prior art carbonation step, respectively.
Figure 17:
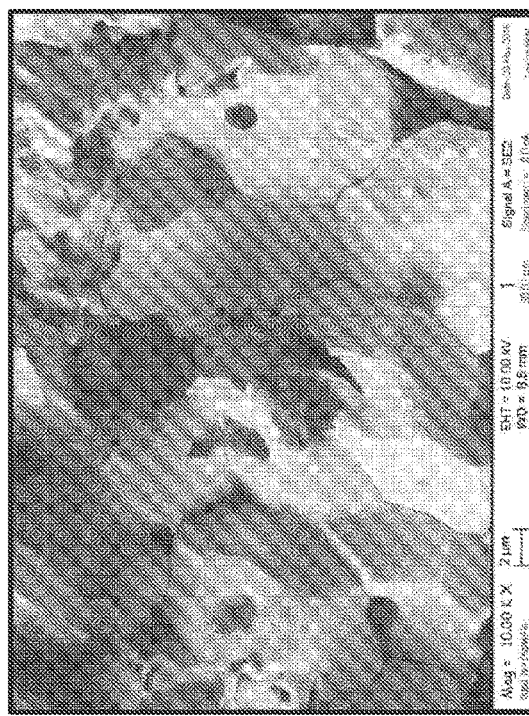
Figure 17:
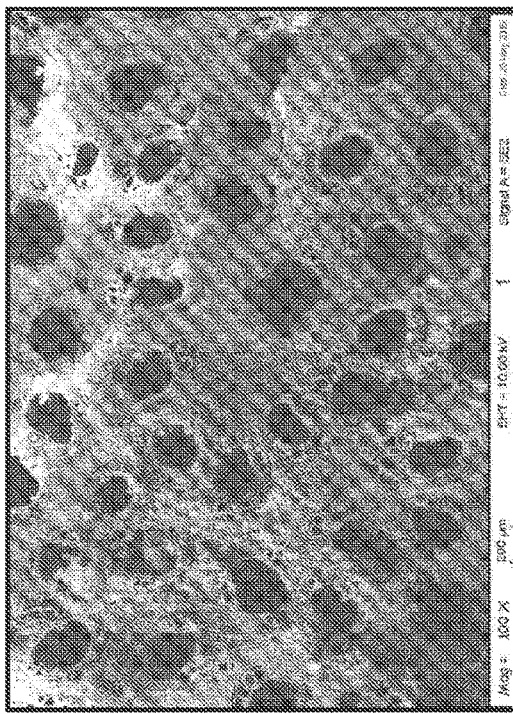
Figure 17:
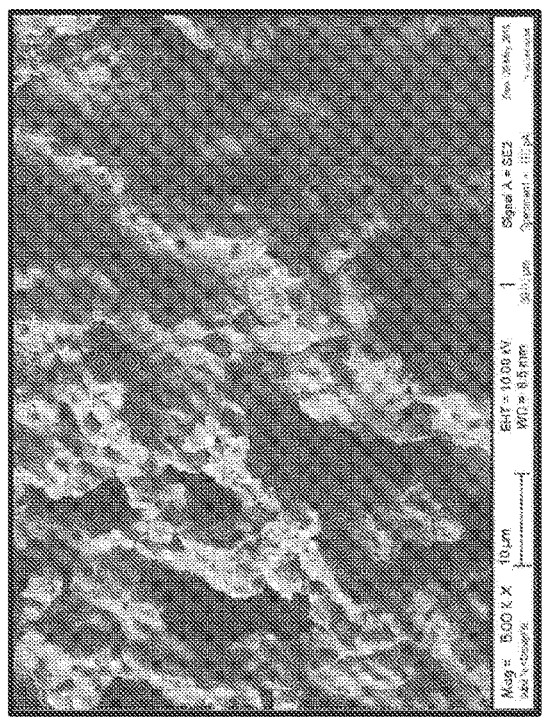
Figure 18:
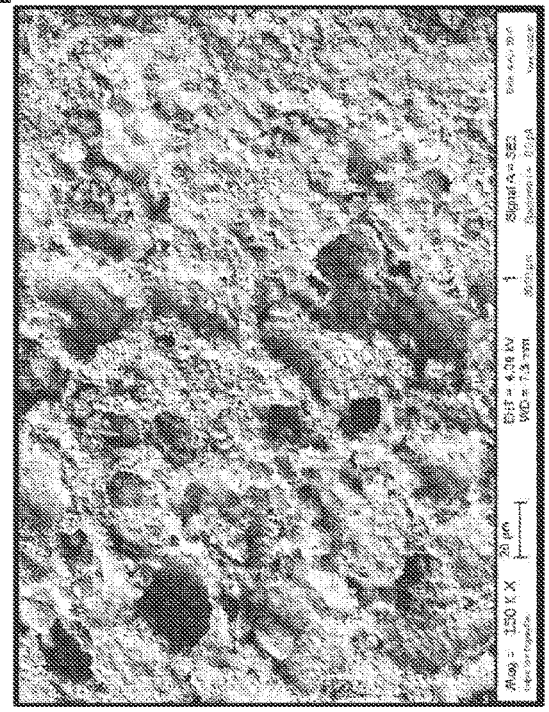
Figure 18:
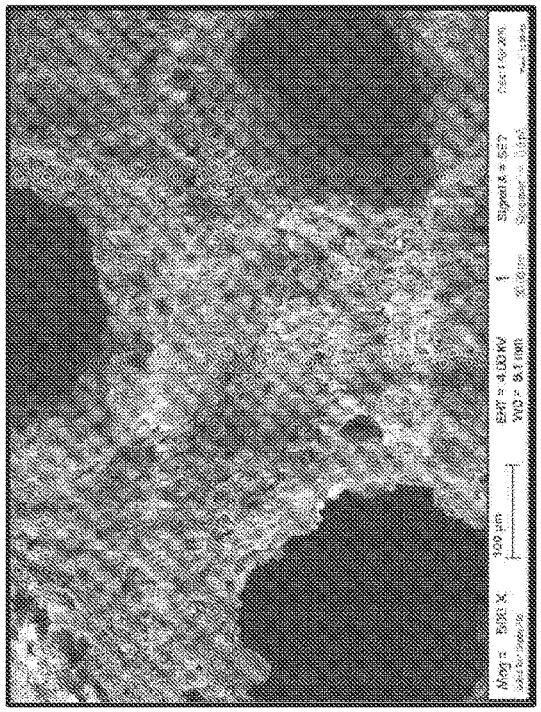
Figure 18:
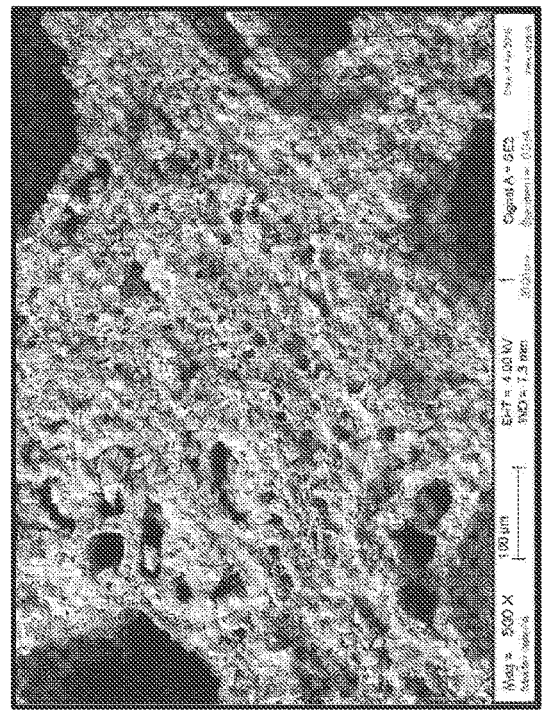
Figure 18:
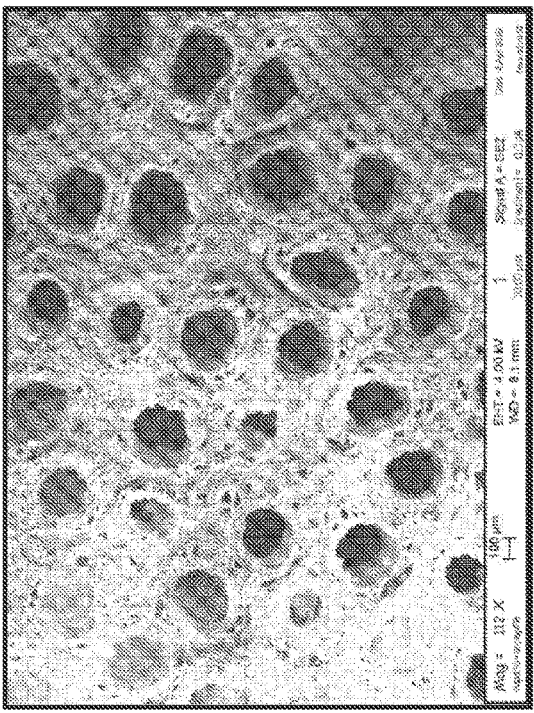

The carbonation process occurs through the formation of reactive intermediates, such as calcium hydroxide. This leads to a final calcium carbonate characterized by a fine-grained structure substantially free of any large cubic crystal of calcium carbonate (>10 μm), which might compromise the structural integrity of the 3D structure. Comparative example 4 and FIGS. 17-18 show that, thanks to the application of a hydration step, after the carbonation step a finer-grained structure is obtained, compared to the intermediate 3D structure that is obtained with the processes known in the art.

The carbonation step carried out in the conditions described above results in superior mechanical properties of the biomorphic hydroxyapatite scaffold obtainable by the process of the disclosure when compared to similar processes known in the art, in which the carbonation step is carried out at high temperature and low pressure or at high pressure and low temperature.

The inventors of the present patent application have surprisingly found that the achievement of the above reported features in the calcium carbonate is an important condition to enable the complete transformation of large pieces (i.e. ≥2 cm) into a final biomorphic scaffold having the desired composition and maintenance of the original wood microstructure.

In the phosphatization step 6) of the multi-step process, the at least one phosphate salt may be selected from the group consisting of ammonium phosphate, sodium phosphate, and potassium phosphate. The use of ammonium phosphate enables a better control of the pH, hence the conversion process is more efficient and the resulting body has favorable mechanical properties and physical cohesion.

In the phosphatization step of the multi-step process, the calcium carbonate template may be immersed in a solution comprising at least one of said phosphate salts. The solution may have a concentration of 0.1 to 5M, preferably a concentration of 0.5 to 2.0M.

The starting ratio of $PO_4/CO_3$ in the phosphatization step of the multi-step process is preferably 1.5 to 5 times the theoretical stoichiometric value, preferably 2 to 4 times the theoretical stoichiometric value.

In the phosphatization step of the multi-step process, the calcium carbonate template immersed in a phosphate-rich solution may be heated from 25° C. to 300° C. under a vapour pressure in the range of 0.1 to 2.5 MPa (hydrothermal conditions).

The phosphatization step may last about 12 to about 180 hours, preferably about 48 to about 120 hours, more preferably from 24 to 72 hours.

The starting pH of the phosphate-rich solution in the phosphatization step of the multi-step method is preferably between pH 7 and 12.

Substitution of the hydroxyapatite with other ions can be achieved by introducing suitable soluble salts containing the ions of interest during or after the process completion, preferably during the phosphatization process. Suitable ions may include strontium, magnesium, silicon, titanium, carbonate, sodium, potassium, gallium, silver, copper, iron, zinc, manganese, europium, gadolinium, and mixtures thereof. An example of a solution containing magnesium ions is $MgCl_2.6H_2O$, and an example of a solution containing strontium ions is $SrCl_2.6H_2O$.

As a consequence of the ionic doping, the final biomorphic scaffold comprises or consists of a material comprising or consisting of doped hydroxyapatite and tricalcium phosphate.

According to a less preferred embodiment, where the native wood has not been shaped into form and dimensions suitable for being used as bone substitute (i.e. if step i) is not carried out), the biomorphic hydroxyapatite scaffold obtained from the multi-step process may conveniently be shaped into a scaffold having the required form and shape by known techniques.

The disclosure relates also to the biomorphic hydroxyapatite scaffold obtained (or obtainable) from the process described above, having improved physical and mechanical properties if compared to hierarchically structured hydroxyapatites obtained by similar processes known in the art.

In particular, the biomorphic hydroxyapatite scaffold obtained (or obtainable) from the process of the present disclosure possess all the features above described for the scaffold or bone substitute of the disclosure.

In particular, with respect to the prior art, the final biomorphic scaffold obtained with the process here described possess a porosity which is composed by a higher percentage of micro and nano-pores than the scaffolds obtained by similar processes known in the art. In particular at least 25% of the total porosity, preferably between 25% and 50% of the total porosity of the hydroxyapatite scaffold of the disclosure is due to pores having a diameter≤1 µm, preferably ≤0.1 µm, in particular between 0.01 and 0.1 µm.

This high percentage of micro and nano-porosity is extremely advantageous from a clinical point of view because micro and nano-pores permit exchange of nutrient fluids and discharge of the waste products of cell metabolism enhance, thus improving bone regeneration.

Moreover, the biomorphic scaffold of the disclosure shows a higher specific surface area (9 to 20 m²/g vs 5-6 m²/g) than a scaffold obtained with a process known in the art. A higher surface area determines enhanced surface bioactivity and enhanced wettability of the scaffold or bone substitute, thus improving the osteointegration and bio-resorption process.

Also the biomorphic scaffold of the disclosure includes hydroxyapatite grains of about 100-200 nm (i.e. nano-grains), much smaller than the ones present in sintered hydroxyapatite (i.e. typically >1 pun). Small grains show a clinical advantage for bone regeneration because they can be more easily resorbed by the cells, thus allowing a better bone regeneration with respect to the scaffold known in the art.

In addition, the biomorphic scaffold of the disclosure exhibits compressive strength greater than 5 MPa, preferably between 10 MPa and 20 MPa, measured in the direction along the channel-like pores (longitudinal direction), and a compressive strength along the direction of the transversal channels (transversal direction) of up to 10 MPa. The inventors of the present disclosure surprisingly found that these mechanical features make the final hydroxyapatite scaffold as a stand-alone material, therefore it can be applied in procedures of regeneration of load-bearing bone parts without the use of any reinforcing or sustaining structure such as shells or bars.

In nature, nanocrystalline, ion-substituted hydroxyapatite is the main component present in hard body tissues; in fact, the mineral phase in bone is a nanostructured phase composed of finely dispersed hydroxyapatite platelets of dimensions below 100 nm that organize in a 3D hierarchically organized porous structure representing the whole bone tissue.

In this respect, the inventors of the present disclosure surprisingly found that, when compared with previously known art, the biomorphic transformation of natural wood structures obtained by the above described process, can uniquely give rise to final hydroxyapatite bone scaffolds exhibiting simultaneously bone-mimicking composition, high open and interconnected macro/micro/nano-porosity and superior mechanical strength, associated with a size relevant for application in load-bearing sites, particularly in long segmental bones of the limbs, or large maxillofacial regions, or in spine.

All these features, which have never been shown to occur simultaneously, are of outmost importance to enable extensive bone regeneration in load-bearing sites. The differences in the biomorphic hydroxyapatite scaffold structure obtainable with the process according to the present disclosure yield important clinical advantages that are shown in comparative example 6. In particular, the present scaffolds show a higher inductive power on the expression of osteogenic related genes, with respect to the prior art scaffolds, which translate in a better clinical performance in terms of bone regeneration.

The present disclosure is further illustrated by the following, non-limitative, examples.

EXAMPLES

Methods of Measurement

Total Porosity of Wood Subjected to a Pyrolysis Step (Pyrolized Wood):

A piece of pyrolyzed wood, shaped as a prism or a cylinder, is weighed, then the volume is obtained by measuring diameter and height. The absolute density (A.D.) of the pyrolyzed wood is obtained by weight/volume ratio; the relative density (R.D.) is obtained by dividing the A.D. of the pyrolyzed wood by the theoretical density of carbon (i.e. R.D.=A.D./2.25). The total porosity (%) is obtained by (1−R.D)*100.

Total Porosity of a Scaffold Obtained after Each Step of the Process and of the Biomorphic Hydroxyapatite Scaffold Obtained at the End of the Process:

The porosity is calculated by applying the same method as above using appropriate values for the theoretical density of each material obtained after each step (i.e. the theoretical density of $CaC_2$, CaO, $CaCO_3$, HA).

Compressive Strength:

the final scaffold or bone substitute, shaped as a prism or a cylinder, is subjected to loading by using a universal screw-type testing machine to obtain stress-strain curves and the fracture load. The compressive strength is given by the ratio between the fracture load and the area subjected to compression.

Pore Diameter:

the pore size distribution and pore morphology of the final scaffold or after each step of the process are evaluated by means of mercury intrusion porosimetry and scanning electron microscopy (SEM), respectively. Mercury intrusion porosimetry analysis is based on the measure of the intrusion of mercury into the pores of the sample at various pressures.

Crystalline Phases: Identification and Quantification:

of the crystalline phases on scaffolds are performed by X-ray powder diffraction technique (XRD), evaluating the result of the X-radiation incidence on the sample, with different and continuous angles.

Specific Surface Area:

the total surface area of the materials per unit of bulk volume (m²/g) is evaluated using the BET method, estimated from the amount of gas adsorbed in relationship with its pressure.

Example 1

Preparation of a Hydroxyapatite Derived from Wood Using the Multi-Step Process i) A piece of native rattan wood is shaped in a cylindrical form having the following dimensions: diameter=2 cm; height=3 cm;

1) Pyrolysis of the Native Wood

The starting wood piece is dried at 70° C. for 24 hours, then treated at 800° C. for more than 30 minutes under flowing nitrogen, thus transforming into pure carbon template. Thermal cycle: heating at 1° C./min up to 350° C. and 2° C./min from 350° to 800° C. The sample is maintained at temperature of 800° C. for about at least 30 min and subsequently the template is cooled at 1° C./min.

2) Carburization

The carbon template is subjected to heating at 1000° C. under argon and calcium atmosphere at 0.5 mbar, thus transforming in calcium carbide. Dwell time at 1000° C.=30 minutes.

3) Oxidation

The calcium carbide template is heated in air up to 1100° C. following a heating rate in the range of 1–7° C./min, thus enabling the complete transformation into calcium oxide.

4) Hydration

The calcium oxide body is activated by exposure to water, thus enabling water uptake in the amounts of about 10 mole %.

5) Carbonation

The pre-conditioned hydrated body is heated to 800° C. under a progressively increasing $CO_2$ pressure of 0.5 to 10 MPa. This transforms the calcium oxide body into calcium carbonate.

6) Phosphatization

The calcium carbonate body is immersed in a 0.5 M ammonium phosphate solution and a starting $PO_4$ to $CO_3$ ratio of 2 times the theoretical stoichiometric value, at a temperatures of 200° C. under a water vapor pressure of 2 MPa.

The compressive strength of the scaffold was evaluated by exerting mechanical forces along the perpendicular and transversal direction, with respect to the orientation of the channel-like pores.

Figure 3:
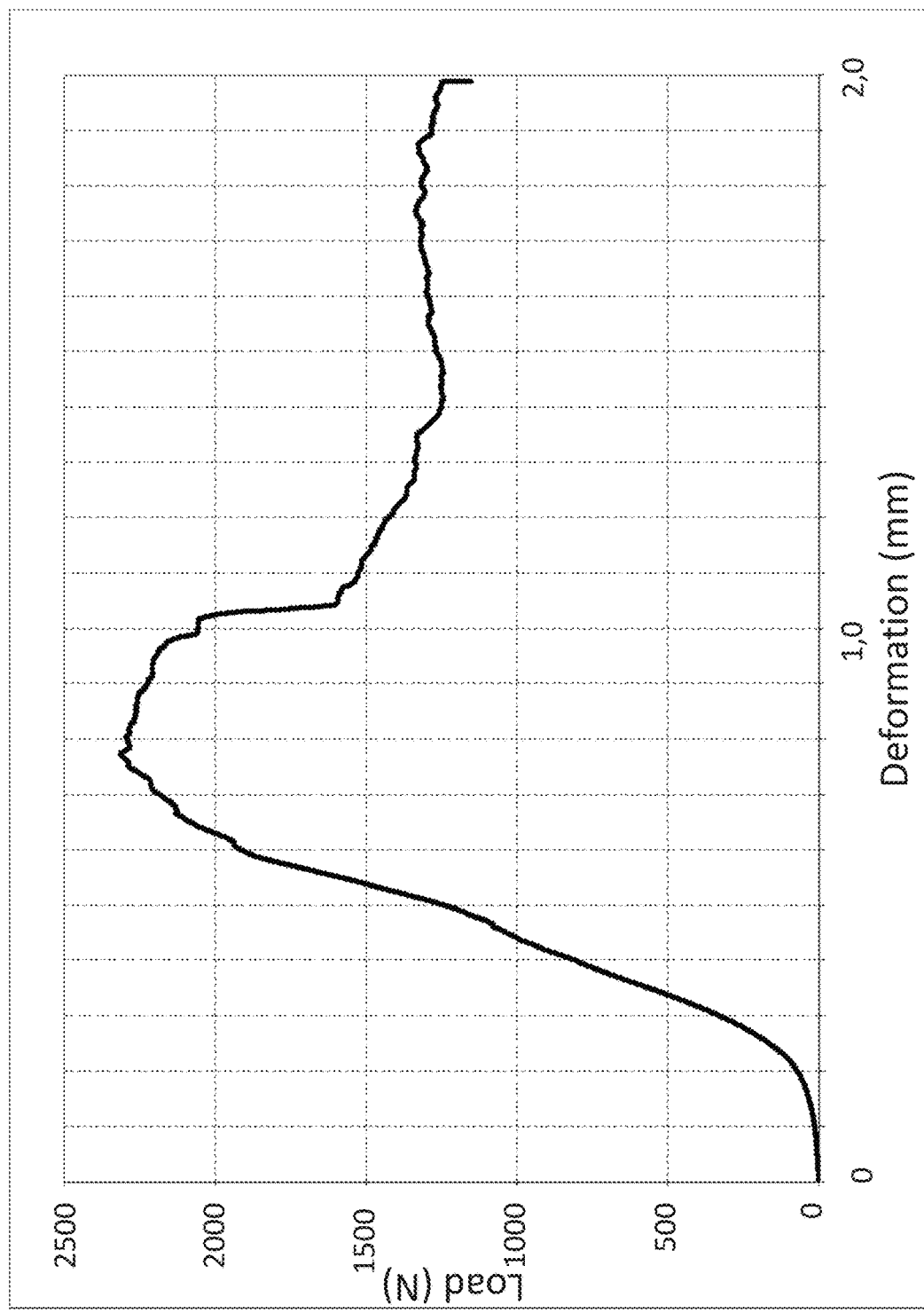
FIG. 3 shows a stress-strain curve of a biomorphic scaffold subjected to compressive loading, wherein y=stress (N), and x=strain (mm).

By loading along the pore direction (which is the most clinically-reflective configuration to mimic the in vivo biomechanical stimuli in the case of long segmental bones), the scaffold (developed as a hollow cylinder with outer diameter=15 mm; inner diameter=6 mm height=20 mm, and a pore extent of 60-65 vol %) exhibited compressive strength of up to 16 MPa (i.e. 250 Kg of ultimate load (FIGS. 1 and 3). In the transversal direction, the scaffold exhibited compressive strength of up to 4 MPa.

The scaffold could also be subjected to thermal treatment at a maximum temperature of 1300° C., in a controlled atmosphere, to further increase the mechanical strength of the scaffold.

The bone-like microstructural features of the biomorphic scaffold enables delivery of topological information to cells to build new bone tissue with organized structure. This was confirmed by in vivo tests where the scaffold was implanted in rabbit femurs and mouse calvaria.

The scaffold did not induce any toxic adverse reactions nor any necrosis or infections after surgery. The scaffold yielded extensive colonization by the newly formed bone after 1 month, similar to the control which was a commercial porous apatite scaffold: EngiPore, Finceramica S.p.A., Italy.

The tissues explanted from mice calvaria showed extensive bone formation and penetration into the scaffold pores both when the scaffold was implanted alone and also when osteogenic stromal cells were added to the implanted scaffold (FIG. 2a-d). The channel-like porosity of the scaffold induced the formation of bone structures mimicking Haversian systems (as indicated by the arrows in FIG. 2f). Moreover, the channel-like pores of the scaffold induced fast angiogenesis so to assist the formation and penetration of the new bone. This result confirms that a suitable orientation of the porosity in relationship to the orientation of the endogenous vascular network can be effective in promoting early development of extensive angiogenesis.

Example 2

Comparison of Biomorphic Hydroxyapatite of the Disclosure and Hierarchically Structured Hydroxyapatite Known in the Art A comparison test was made between the pore size distribution of biomorphic hydroxyapatite of the present disclosure obtained from rattan native wood and the pore size distribution of a hierarchically structured hydroxyapatite obtained from the same native wood according to the teaching of Anna Tampieri et al. in the *Journal of Material Chemistry*, 2009, 19, 4973-4980 using the teaching of Ruffini et al. in Chemical Engineering Journal 217 (2013) 150-158 for the phosphatization step only (Mixture of $NH_4H_2PO_4$—$(NH_4)_2HPO_4$, pH=9, Tmax=60° C., time=80 h).

Figure 4:
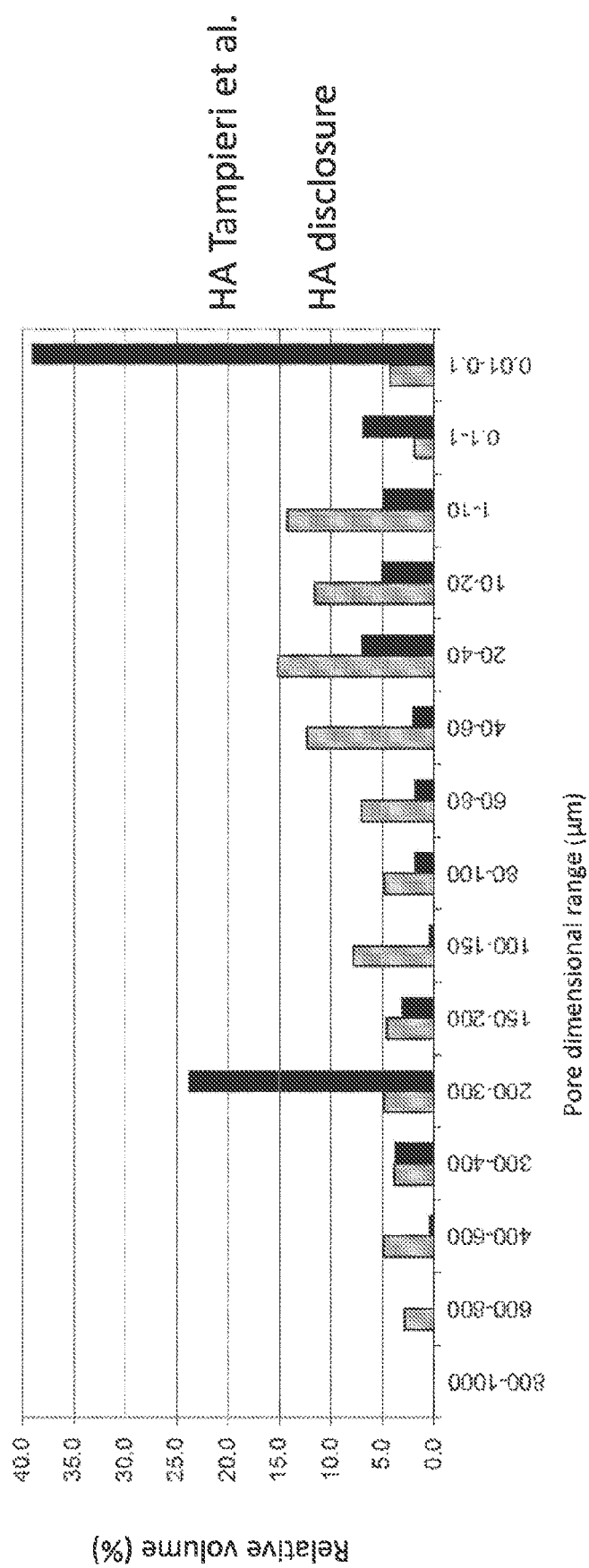
FIG. 4 shows the distribution of internal pore volume of the biomorphic hydroxyapatite of the present disclosure compared with the pore volume of the hierarchically structured hydroxyapatite obtained with a method known in the art.

The results are shown in FIG. 4, wherein the black columns refer to the biomorphic hydroxyapatite of the disclosure and the dark gray columns to the hydroxyapatite known in the art.

It is evident the increasing in the number of pores having diameter comprised in the range 200-300 μm in the biomorphic hydroxyapatite of the present disclosure in comparison with known hierarchically organized hydroxyapatite, said pores being the ones with the most appropriate dimensions to promote a physiological vascularization of the biomorphic hydroxyapatite when implanted as bone substitute.

Moreover, the same FIG. 4 shows an increasing number of pores having diameter in the range 0.01-0.1 micron, which clearly indicates that the microstructure of the native wood is preserved in the final product.

Example 3

Preparation of a Hydroxyapatite Derived from Wood Doped with $Mg^{2+}$ and/or $Sr^{2+}$ Steps 1 to 5 of the multi-step method as described in example 1 are followed to yield the calcium carbonate body. Doping with $Mg^{2+}$ and/or $Sr^{2+}$ ions has been achieved according to each of the following methods:

Method 1

A solution of $Sr^{2+}$ (in the form of SrCl) is added to a 1.0 M phosphate-rich solution. The calcium carbonate body prepared according to the multi-step method is then immersed in the combined solution and heated to a temperature of 200° C. under a water vapor pressure of 2 MPa. This yields a $Sr^2$-doped hydroxyapatite with the morphology of the starting wood piece.

Method 2

The calcium carbonate body is immersed in 1.0 M phosphate-rich solution. Whilst heating to a temperature of 25-90° C. under a water vapor pressure of 0.1 MPa, a solution $Sr^{2+}$ is progressively added. This yields a $Sr^2$-doped hydroxyapatite with the morphology of the starting wood piece.

Method 3

The pure calcium carbonate body (or partially converted in hydroxyapatite by immersion in 1.5 M phosphate-rich solution at room temperature or higher for 24 h) is immersed in an aqueous or organic solution containing $Sr^{2+}$ ions for 24 h. It is then removed from the solution and is immersed in 1.5 M phosphate-rich solution. Whilst heating to a temperature of 200° C. under a water vapor pressure in the range 0.5-1.5 MPa. This yields a $Sr^2$-doped hydroxyapatite with the morphology of the starting wood piece.

Properties of the Scaffold Substituted with Strontium

Figure 5:
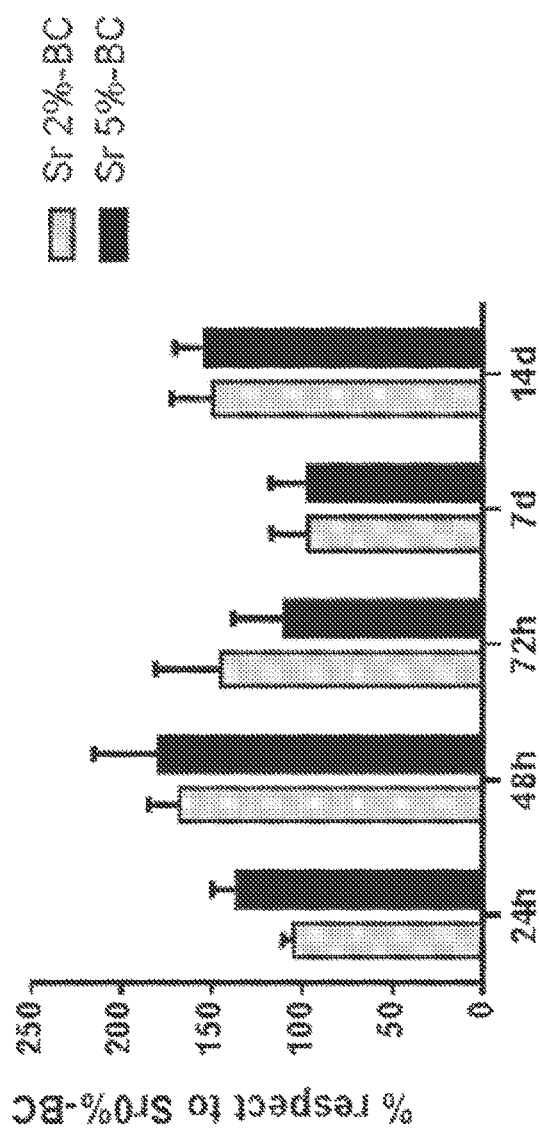
FIG. 5 shows a graph depicting the enhanced viability of mesenchymal stem cells when in contact with scaffolds comprising 2 and 5 mol % of Sr, in comparison with a strontium-free scaffold (BC) after 24 hours, 48 hours, 72 hours, 7 days and 14 days. y=% respect to BC.

Hydroxyapatite scaffolds substituted with strontium were developed and were found to exhibit enhanced viability of mesenchymal stem cells (MSCs) when compared to the strontium-free scaffolds (FIG. 5).

Figure 6:
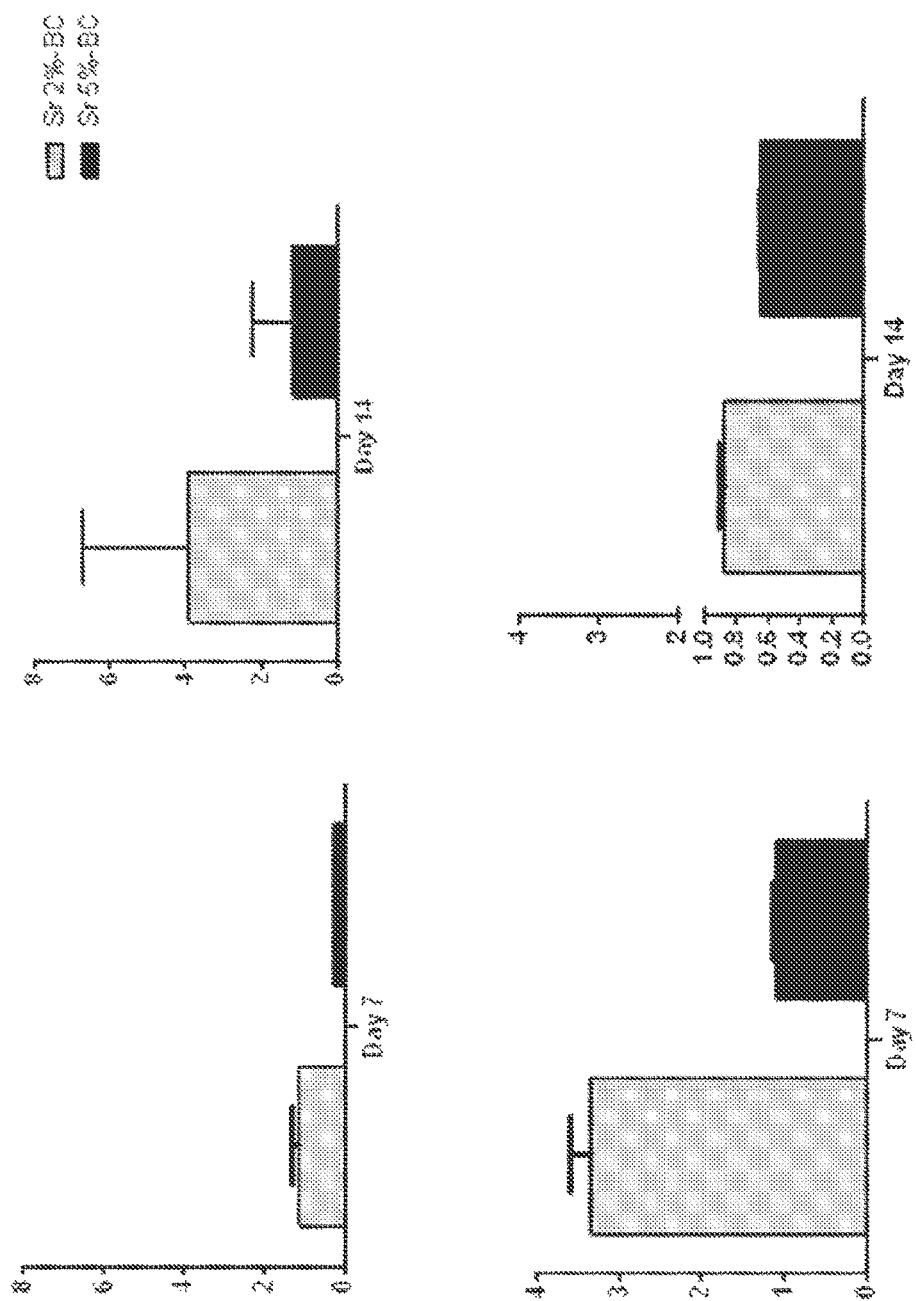
FIG. 6 shows graphs depicting the expression of osteogenesis-relevant genes, such as (a) RUNX2 and (b) ALP in scaffolds containing 2 mol % (Sr2%-BC) and 5 mol % (Sr5%-BC) of strontium. y=fold-change expression relative to BC and x=days.

The strontium scaffolds also displayed well-spread morphology and increased expression of osteogenesis-relevant genes, such as RUNX2 and ALP (FIG. 6), thus acting as promoters of osteoblastic differentiation. In particular, when compared to the Sr-free scaffold, a significant increase in mRNA level of both the genes ($p<0.05$) was detected. This increase was particularly high for the scaffold with 2 mol % of Sr.

Figure 7:
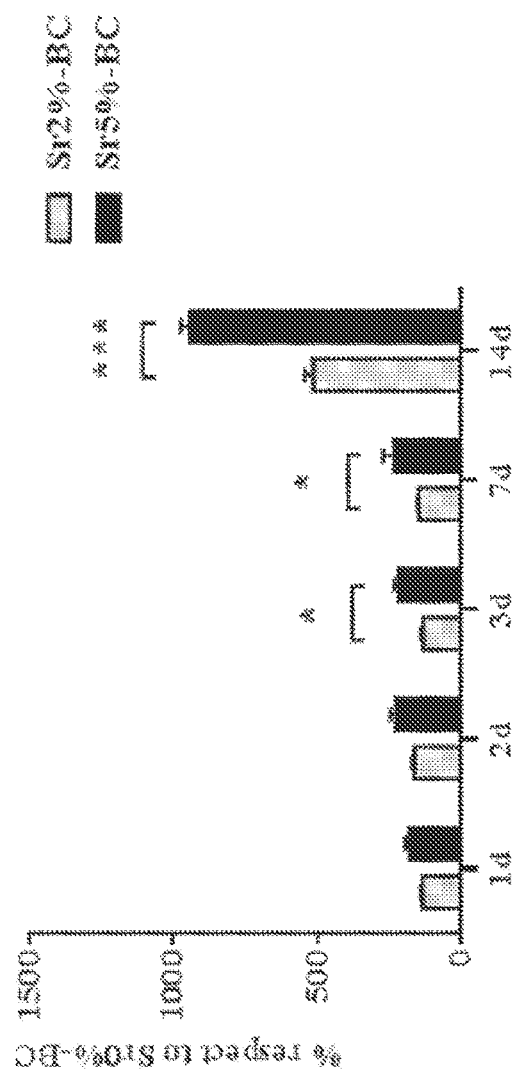
FIG. 7 shows a graph depicting osteoblast viability when in contact with scaffolds comprising 2 mol % (Sr2%-BC) and 5 mol % (Sr5%-BC) of Sr, in comparison with a strontium-free scaffold (BC) after 24 hours, 48 hours, 72 hours, 7 days and 14 days. y=% respect to BC.

Enhanced proliferation of pre-osteoblasts over 14 days of investigation was observed when Sr-substituted hydroxyapatite scaffolds were used (FIG. 7). In fact, an increase of strontium in the scaffold yielded a much higher cell viability in the long term. These results imply that new bone formation could be successfully induced and sustained.

Figure 8:
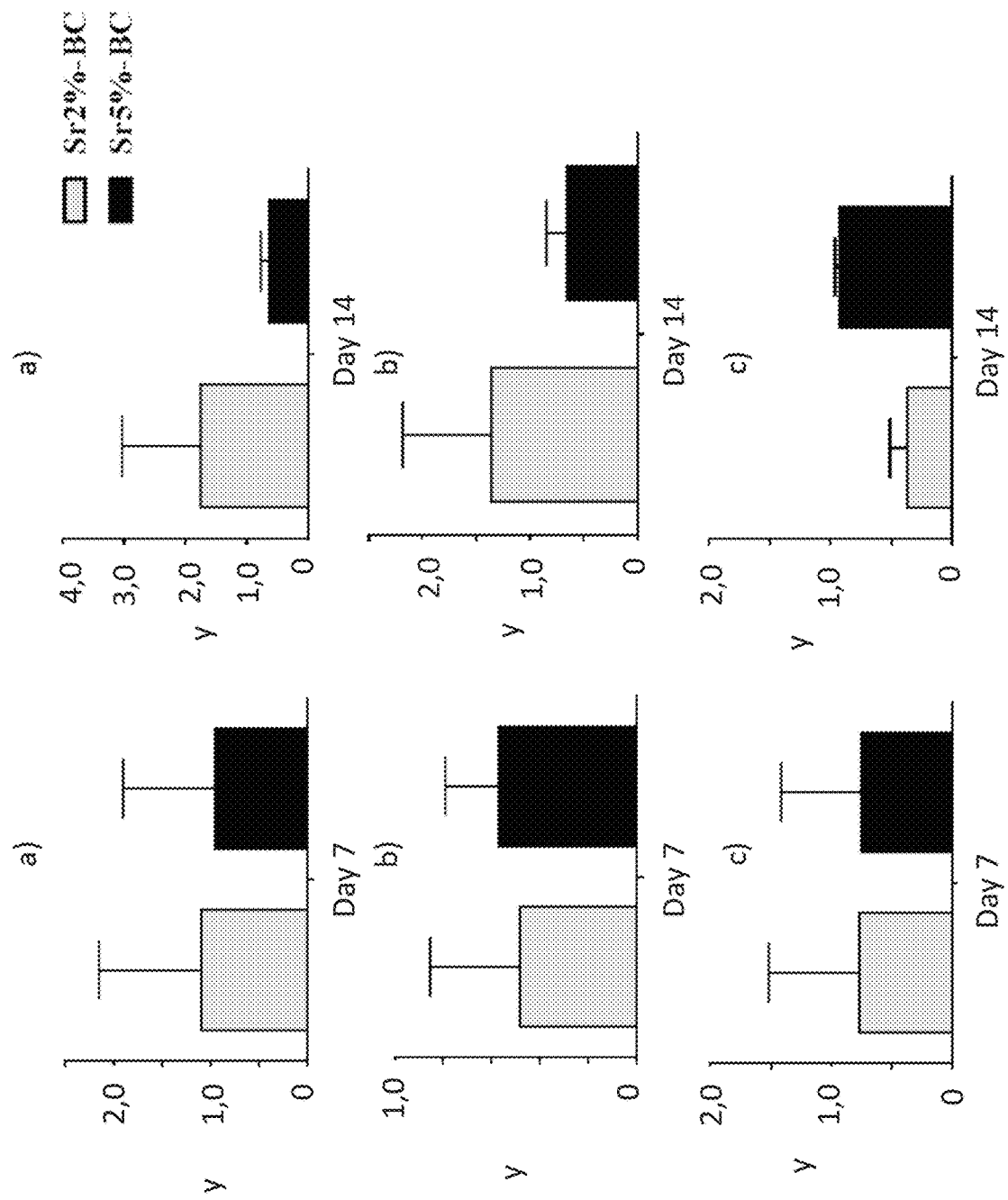
FIG. 8 shows graphs depicting the expression of osteogenesis-relevant genes, such as (a) Osterix, (b) BGlap, and c) IBSP in scaffolds containing 2 mol % (Sr2%-BC) and 5 mol % (Sr5%-BC) of strontium. y=fold-change expression relative to CT and x=days.

The scaffold also demonstrated the possibility of maintaining the osteoblastic phenotype during the two weeks of the investigation (FIG. 8).

The behaviour of cells in contact with the strontium-substituted scaffold was investigated also by observing osteoclast behaviour. A preliminary morphological analysis was carried out to confirm and validate the model of osteoclastogenesis. Osteoclasts grown on the scaffold surface exhibit their typical morphology.

Figure 9:
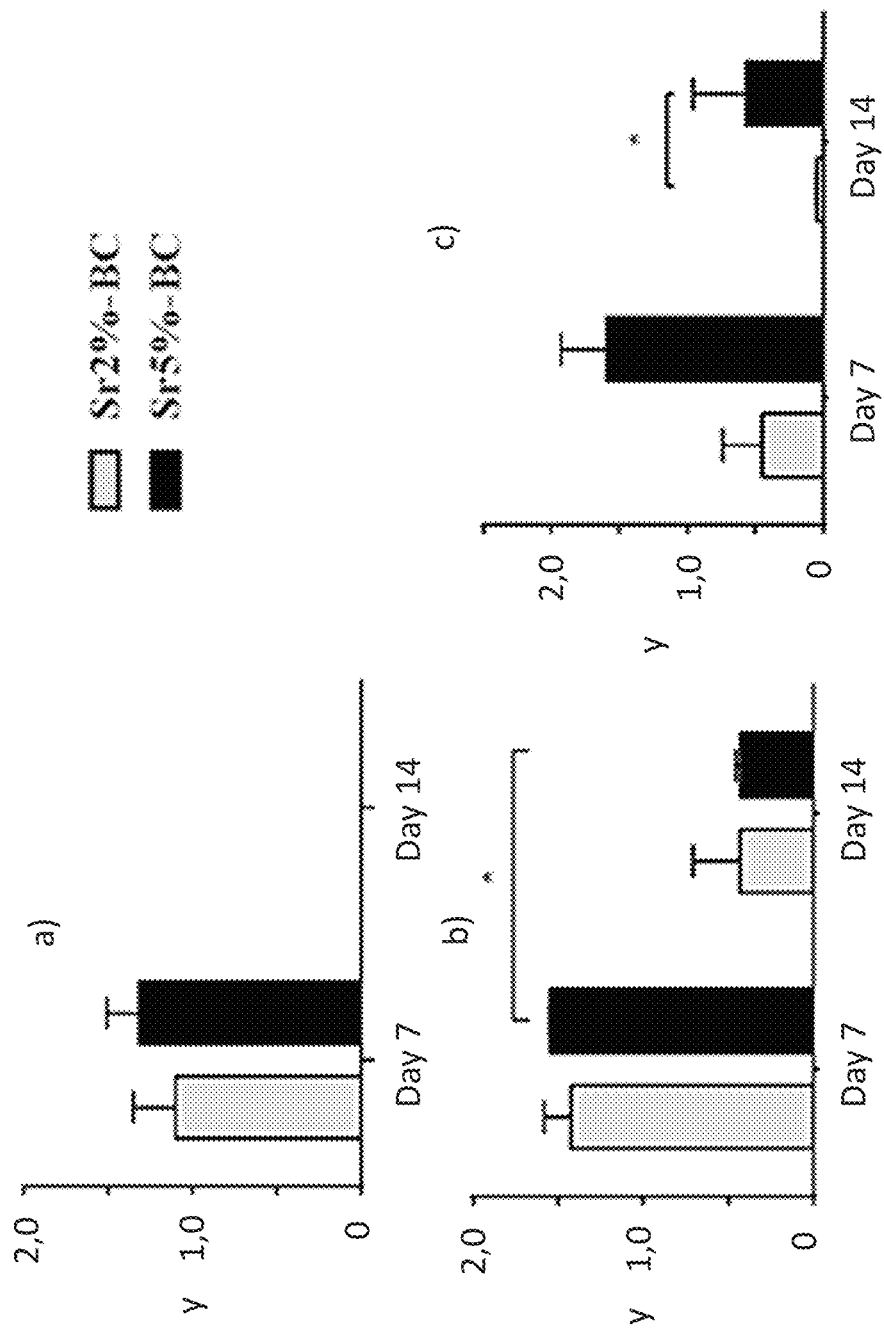
FIG. 9 shows graphs depicting the expression of osteoclast-relevant genes, such as (a) Osacr, (b) CTSK, and c) Itg β3 in scaffolds containing 2 mol % (Sr2%-BC) and 5 mol % (Sr5%-BC) of strontium. y=told-change expression relative to CT and x=days. A significant decrease of the genes involved in the principal molecular pathways of osteoclasts over time can be seen; thus indicating that the presence of $Sr^{2+}$ ions in the scaffold inhibits osteoclast formation and activity; in figure a) the 14 day data were below the detection limit.

The relative gene expression of the principal marker involved in osteoclast activity and formation (Oscar, Integrin β3 and CatepsinK) was evaluated (FIG. 9). The analysis showed a significant decrease in gene expression over time of all the genes involved in the principal molecular pathways of osteoclasts, thus indicating that the presence of $Sr^{2+}$ ions in the scaffold inhibits osteoclast formation and activity.

In conclusion, the substitution of hydroxyapatites with $Sr^{2+}$ ions produced a biological effect on bone cells, specifically causing: i) a significant inductive effect on MCSs osteogenic related genes; ii) an inductive effect on osteoblasts proliferation and iii) an inhibitory effect on osteoclasts activity.

In the case of implantation in a segmental bone defect, the new scaffold is designed to present a central channel that extends in direction parallel to the main unidirectional porosity so to be exposed to the bone stumps as a guide for new bone marrow development (FIG. 1). The channel size is defined on the basis of the specific detect; however, to maintain adequate strength the channel has a diameter in the range 20-60% in respect to the whole scaffold width.

Example 4

Comparison of Biomorphic Hydroxyapatite of the Disclosure and Hierarchically Structured Hydroxyapatite Known in the Art A comparison test was made between a biomorphic hydroxyapatite manufactured using the process of the disclosure and a hydroxyapatite scaffold obtained from the same native wood (rattan) according to the teaching of Anna Tampieri et al. in the *Journal of Material Chemistry*, 2009, 19, 4973-4980. The rattan wood used in the process of the disclosure has a length, measured along a direction in which a dimension of the scaffold is maximum, equal to 2 cm. The rattan wood used in the prior art process has a length, measured along a direction in which a dimension of the scaffold is maximum, equal to 1 cm.

After each step of the two processes, the specific surface area (SSA) and the pore distribution of the intermediate and final scaffolds were analyzed and compared (see FIGS. 10, 16, 19 and 20). In addition, after the carburization step the calcium carbide crystal dimensions of the two intermediate scaffolds were compared (see FIG. 13—bottom pictures).

The crystal lattice structure of the two calcium carbide scaffolds was compared after the carburization step. The comparison is shown in FIG. 14.

Figure 10:
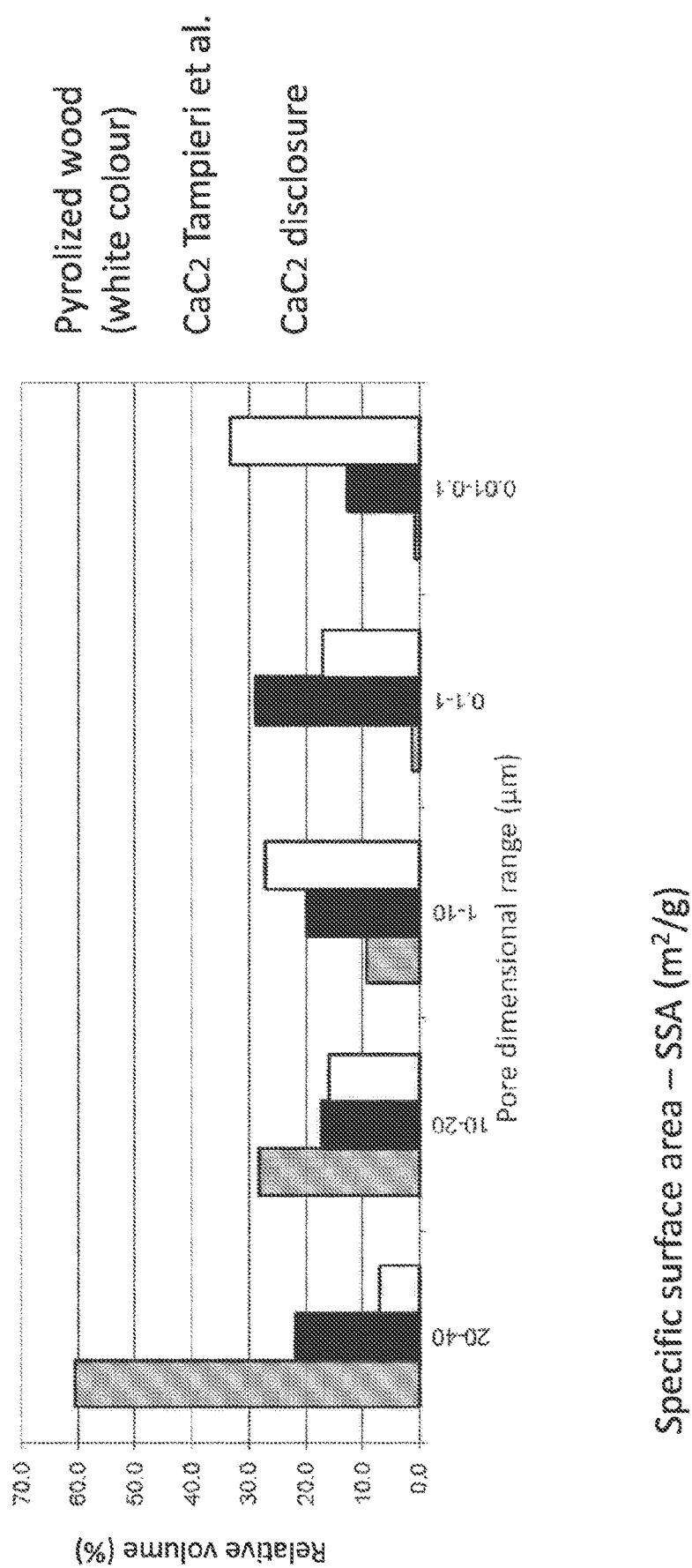
FIG. 10 shows a comparison of the pore distribution of two calcium carbide scaffolds obtained after the carburization step of the prior art and the carburization step of the present invention, further compared with the pore distribution of the starting pyrolized wood. The specific surface area of the two calcium carbide scaffolds are also reported in the figure.

FIG. 10 shows a comparison of the pore distribution of the two calcium carbide scaffolds obtained after the respective carburization steps, further compared with the pore distribution of the starting pyrolized wood. The specific surface area of the two calcium carbide scaffolds are also reported in the figure. The results show that only the calcium carbide scaffold obtained after the carburization step of the disclosure preserves the micro and nano-pore distribution of the rattan wood (pores dimension<1 μm). Also the comparison of the two specific surface areas show an improvement for the scaffold according to the present disclosure.

Figure 11:
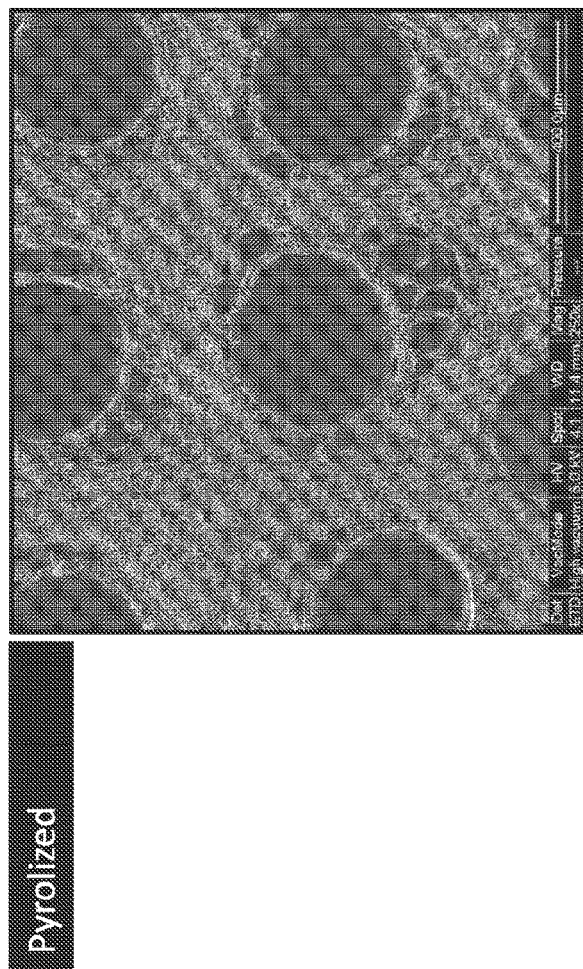
FIGS. 11, 12 and 13—top two pictures show SEM images of two calcium carbide scaffolds obtained with the process of the invention and the prior art process, respectively.
Figure 11:
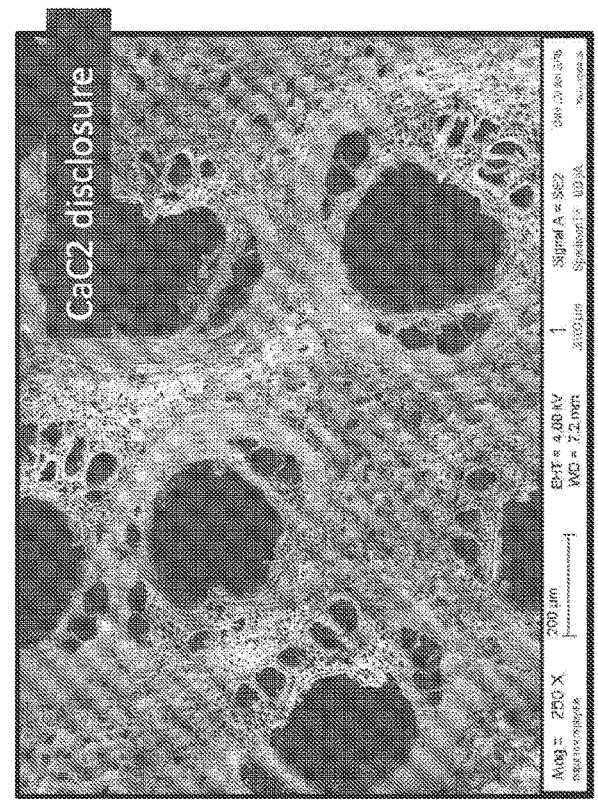
Figure 11:
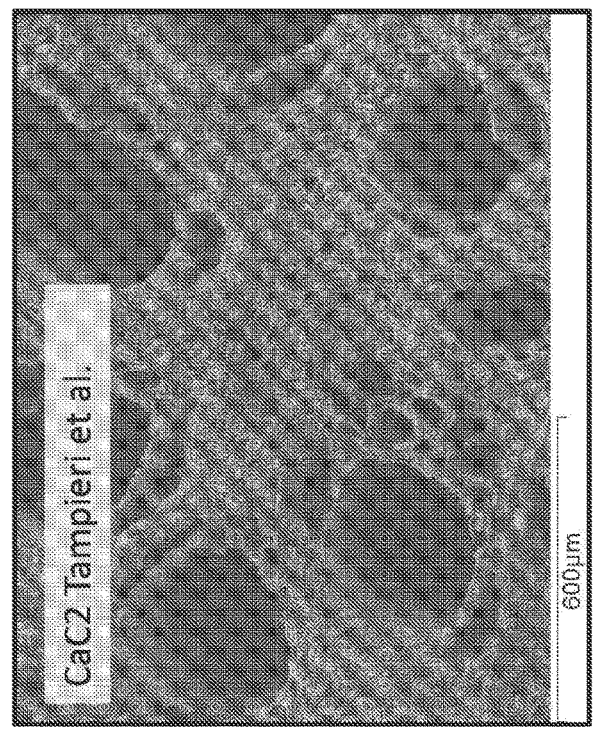
Figure 12:
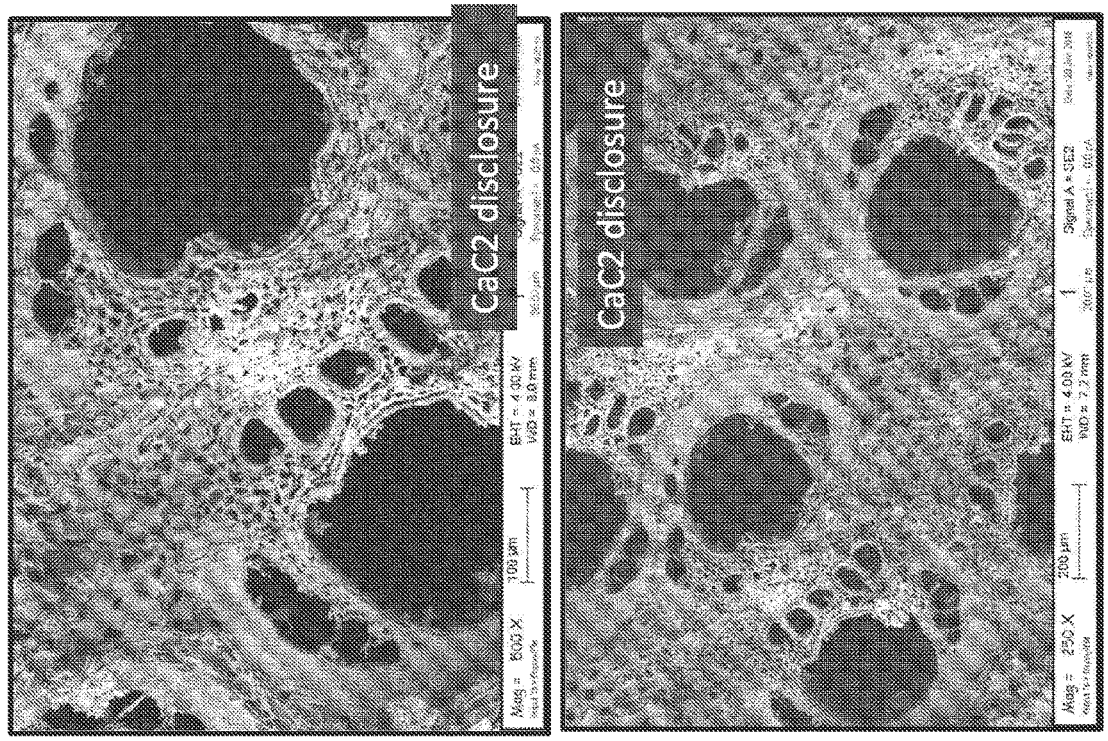
Figure 12:
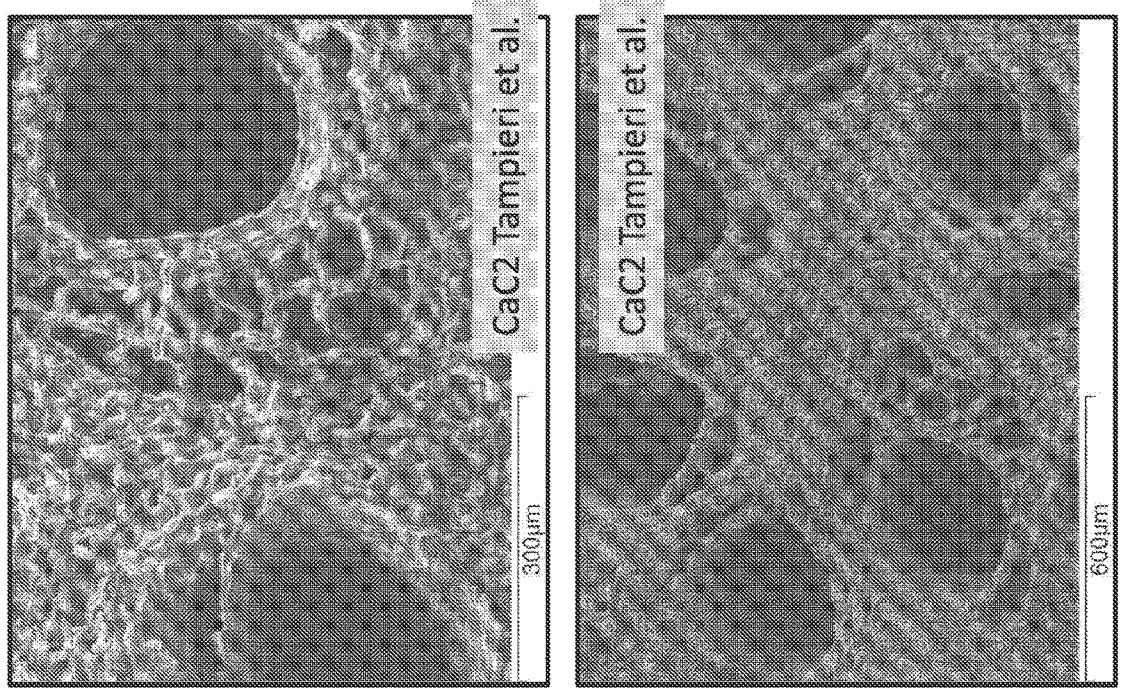

FIGS. 11, 12 and 13—top two pictures show SEM images of the two calcium carbide scaffolds from which the better preservation of the native wood micro and nano-porosity can be clearly seen.

FIG. 13—bottom two pictures show a comparison of the dimension of the carcium carbide crystals. The calcium carbide obtained according to the present disclosure show granes with an average size of about 10 μm, while the granes obtained with the prior art process have an average size of about 100 μm.

FIG. 14 show a comparison of the crystal phase of the two calcium carbide scaffolds, measured with x ray-XRD. The results show that the calcium carbide obtained according to the present disclosure has both a tetragonal and cubic crystal lattice, while the calcium carbide of the prior art has a tetragonal lattice only. The calcium carbide scaffold of the disclosure contains a higher amount of $Ca(OH)_2$ with respect to the prior art scaffold.

Figure 15:
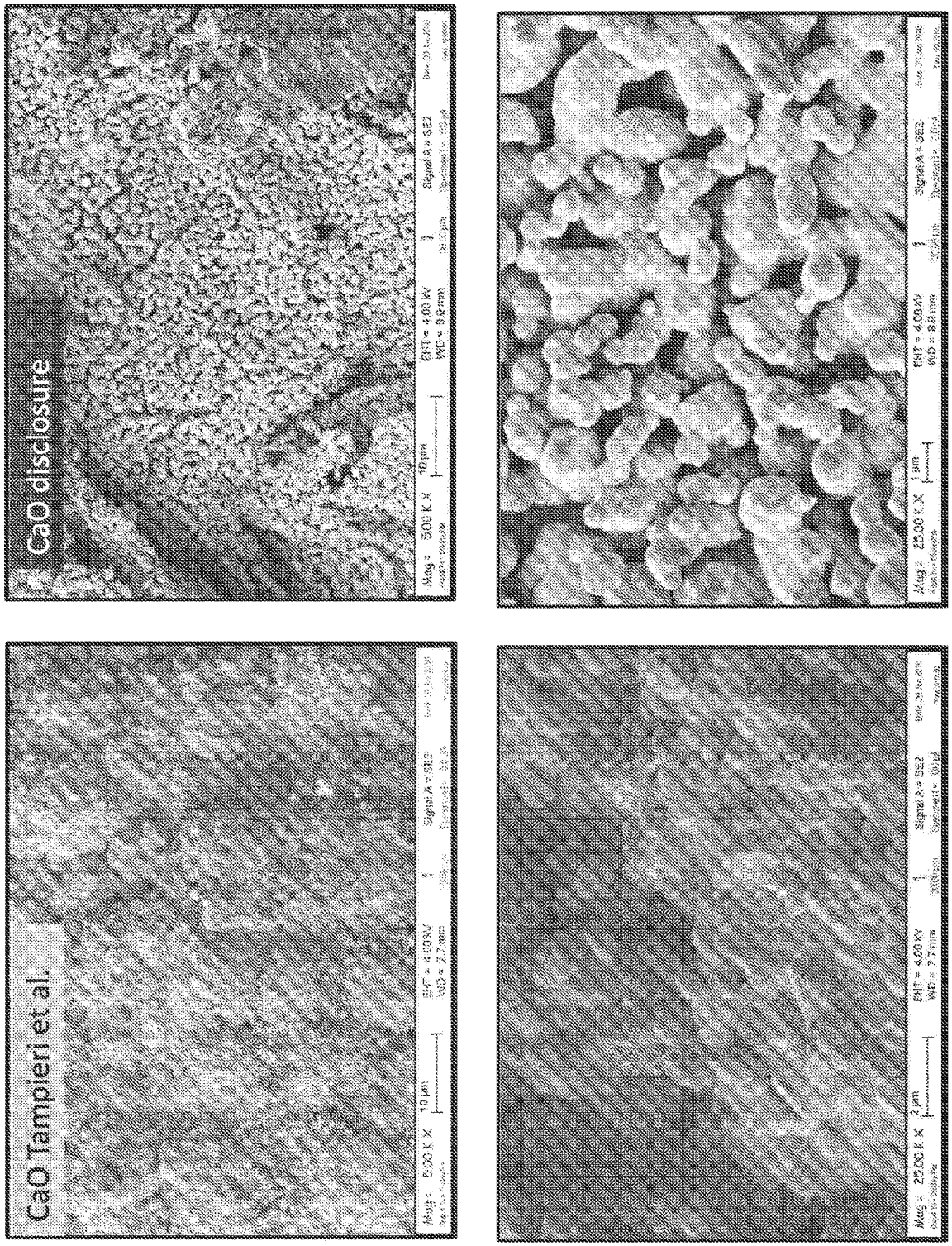
FIG. 15 shows SEM images of the calcium oxide scaffold obtained after the oxidation step of the present invention and the prior art oxidation step.

FIG. 15 shows SEM images of the calcium oxide scaffold obtained after the respective oxidation steps. The pictures corresponding to the scaffold obtained according to the present disclosure preserves a microporosity between the CaO granes, while in the prior art scaffold the microporosity is completely lost.

Figure 16:
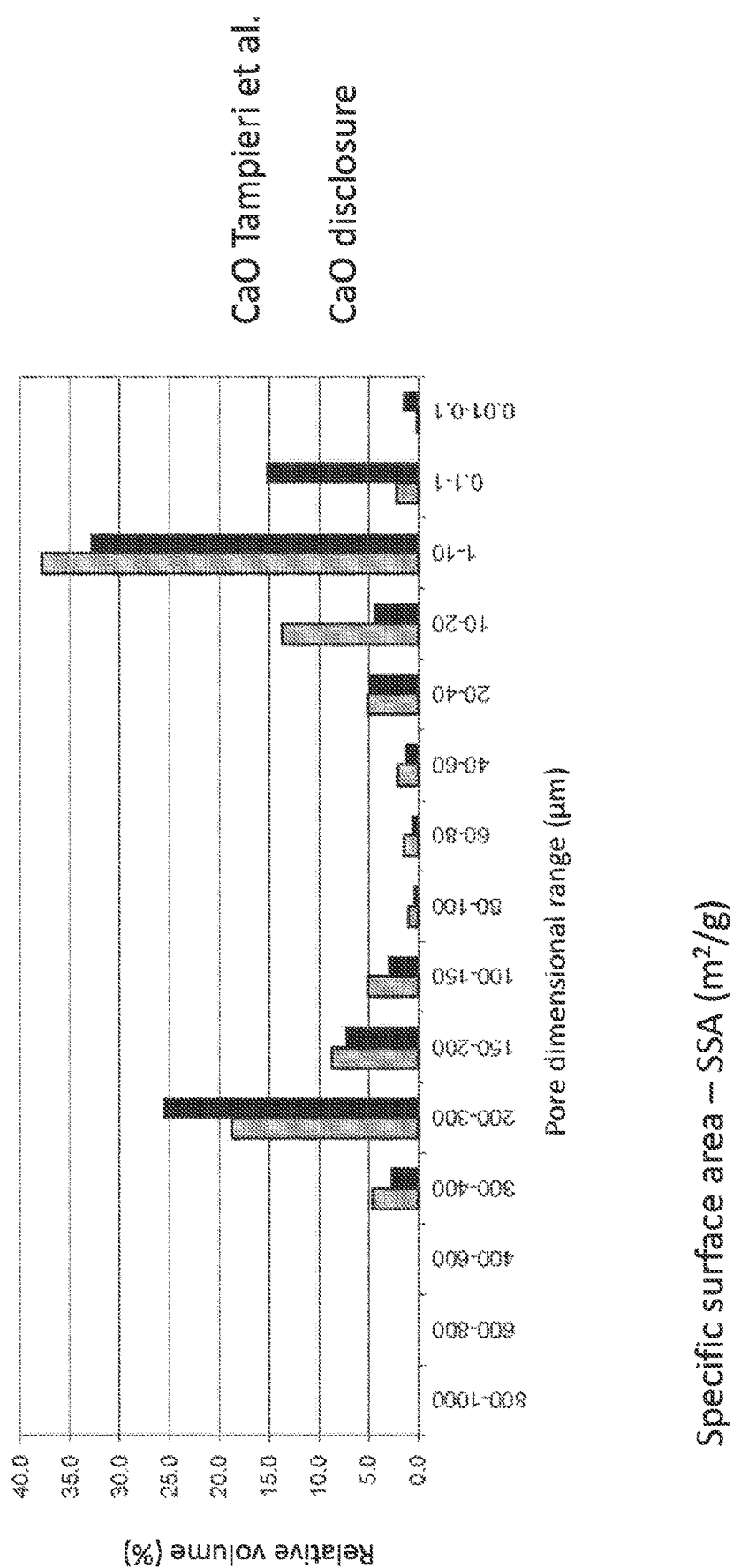
FIG. 16 depicts the pore distribution of the two calcium oxide scaffolds obtained after the oxidation step of the present invention and the prior art oxidation step, respectively.

FIG. 16 depicts the pore distribution of the two calcium oxide scaffolds. The comparison clearly show that the micro and nano-porosity fraction obtained after the oxidation step is higher in the scaffold according to the present disclosure as well as the specific surface area.

FIGS. 17 and 18 show SEM images of the calcium carbonate obtained after the respective carbonation. The material according to the present disclosure show an extended fine structure, compared to the prior art where large crystals of calcite (up to about 50 μm) characterize the whole structure. The large crystals cause the structure to break or collapse during the phosphatization step.

Figure 19:
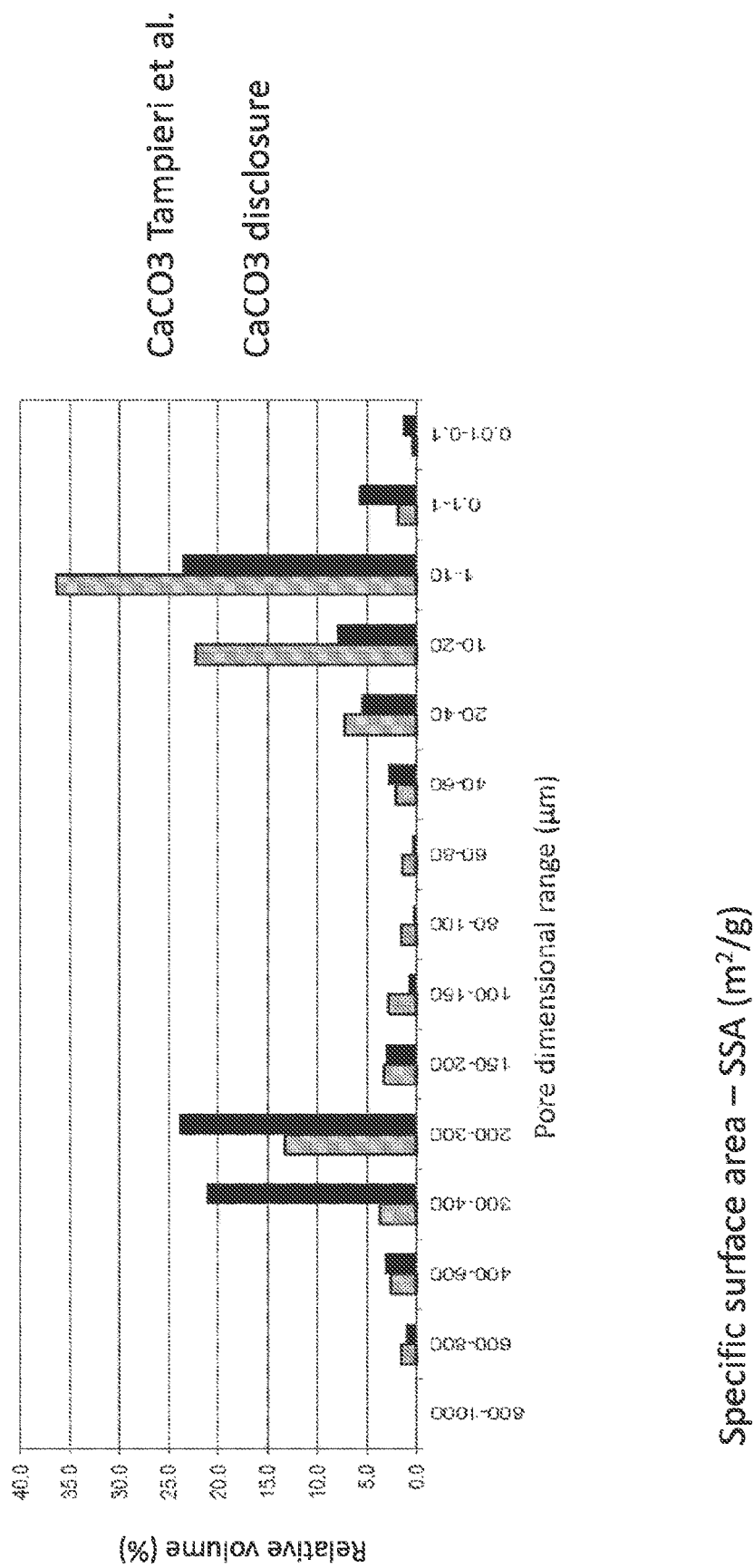
FIG. 19 shows that the pore distribution of the two calcium carbonate scaffolds obtained after the carbonation step according to the present invention and the prior art carbonation step, respectively.

FIG. 19 shows that the pore distribution of the two calcium carbonate scaffolds obtained after the carbonation step. The comparison of the pore distribution and the specific surface area show a result, similar to the one discussed above for the calcium oxide: the micro and nano-pore structure<1 um is maintained with the present process and an higher SSA is obtained with respect to the prior art.

Figure 20:
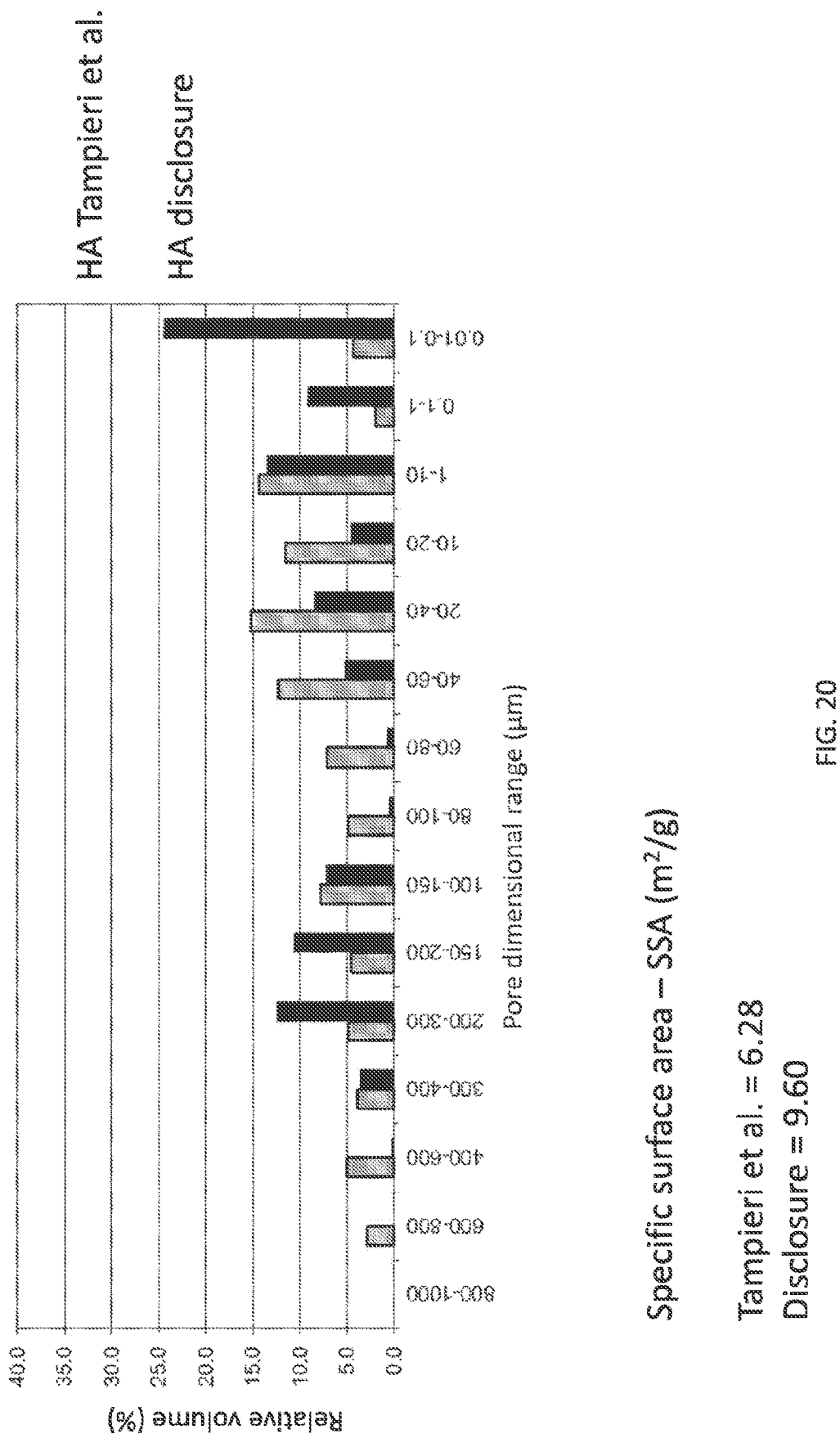
FIG. 20 shows the comparison between the pore distribution of the final biomorphic hydroxyapatite scaffold (after phosphatization) obtained with the process of the disclosure and the final biomorphic hydroxyapatite scaffold of the prior art.

FIG. 20 shows the comparison between the pore distribution of the final biomorphic hydroxyapatite scaffold (after phosphatization) obtained with the process of the disclosure and the final biomorphic hydroxyapatite scaffold of the prior art. A comparison of the respective SSA is also shown.

The results show that the biomorphic scaffold of the disclosure possess a higher micro and nano-porosity fraction than the prior art scaffold as well as a higher specific surface area.

Example 5

Prior Art Process Applied to a Piece of Rattan Wood Having a Length, Measured Along a Direction in which a Dimension of the Scaffold is Maximum, Equal to 2 cm A test was made to demostrate that the prior art process (Anna Tampieri et al. in the *Journal of Material Chemistry*, 2009. 19, 4973-4980) does not allow manufacturing scaffolds having a length, measured along a direction in which a dimension of the scaffold is maximum, equal or greater than 2 cm, i.e. scaffolds of clinical interest for bone regeneration.

To this purpose, a piece of rattan wood has been subjected to the process steps according to the conditions described in Tampieri et al.

Figure 21:
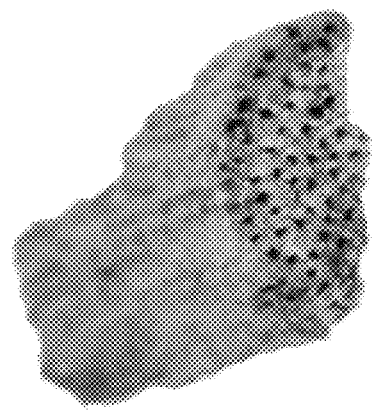
FIG. 21 shows the result obtained after subjecting a piece of rattan wood having a length, measured along a direction in which a dimension of the scaffold is maximum, equal or greater than 2 cm, to the process steps according to the conditions described in the prior art: even before the phosphatization step the scaffold can break down.
Figure 21:
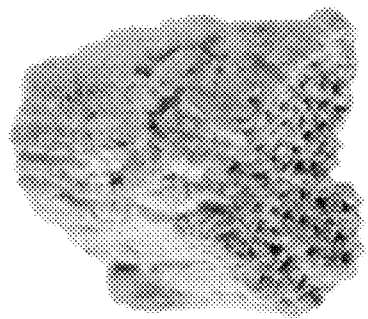
Figure 22:
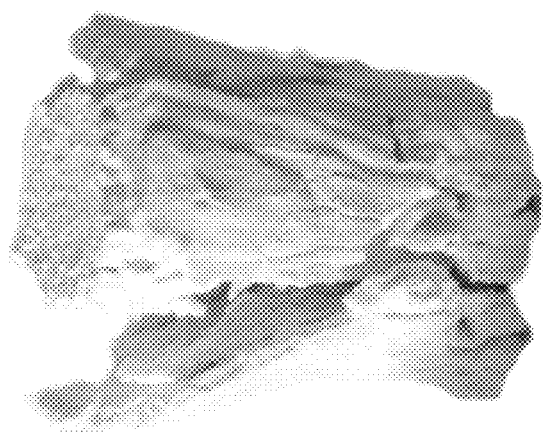
FIG. 22 shows the result obtained alter subjecting a piece of rattan wood having a length, measured along a direction in which a dimension of the scaffold is maximum, equal or greater than 2 cm, to the process steps according to the conditions described in the prior art: even if the scaffold survives the process steps up to phosphatization, after phosphatization the scaffold breaks down.

FIG. 21 show that even before the phosphatization step the scaffold can break down. FIG. 22 show that even if the scaffold survives the process steps up to phosphatization, after phosphatization the scaffold breaks down.

The test clearly shows that the scale up of a ceramic product is often not a straightforward operation; instead the process conditions need to be changed (sometimes heavily changed) in order to prepare larger products, even when a process for making small ceramic product is known in the art.

Example 6

Comparative Test

An in vitro study was performed with mouse mesenchymal stem cell (mMSCs). Gene expression profiling was analysed in order to test the over expression of specific genes involved in osteogenic differentiation induced by a biomorphic hydroxyapatite scaffold obtained with the process of the present disclosure and a biomorphic hydroxyapatite scaffold obtained with the prior art process.

Sample Description

The two tested scaffolds are defined as follows:

|  | Sample |  | | Disk dimension | Number of samples | Sterilization method |
|---|---|---|---|---|---|---|
| Scaffold of the present disclosure | doped (disclosure) | Ca/P = Mg/Ca = Sr/Ca = | 1.65 1.64 0.59 | Ø: 8.00 mm, L: 4.00 mm | 5 | EtOH + UV irradiation |
|  | Not doped (disclosure) | Ca/P = | 1.70 | Ø: 8.00 mm, L: 4.00 mm | 5 | EtOH + UV irradiation |
| Scaffold of Tampieri et al. | Not-doped (prior art) | Ca/P = 1.77 |  | Ø: 8.00 mm, L: 4.00 mm | 8 | 25 kGy γ-ray radiation (GammaRad) |

Results

The genes tested, related to both early (Runx2 and ALP) and late stage (OPN) commitment of osteogenic differentiation, seem to be upregulated in the cells grown in all the disclosure scaffolds compared to the prior art scaffolds, with a significant difference for Runx2 and OPN ($p \leq 0.0001$). No differences were observed in BMP2 and Col15 gene expression in all the samples tested, probably because BMP2, that is the upstream regulator of the differentiation pathway, after 14 days of dynamic culture, it has already carried out its biological function as suggested by the upregulation of Runx2, Alp and OPN [1]. On the contrary, Col15 is a very late marker related to the production of mineralized bone matrix [2] and probably the time of culture was not sufficient to induce its expression. No differences were observed between the inductive effect of the doped or not-doped disclosure scaffolds (see FIG. 23).

Figure 23:
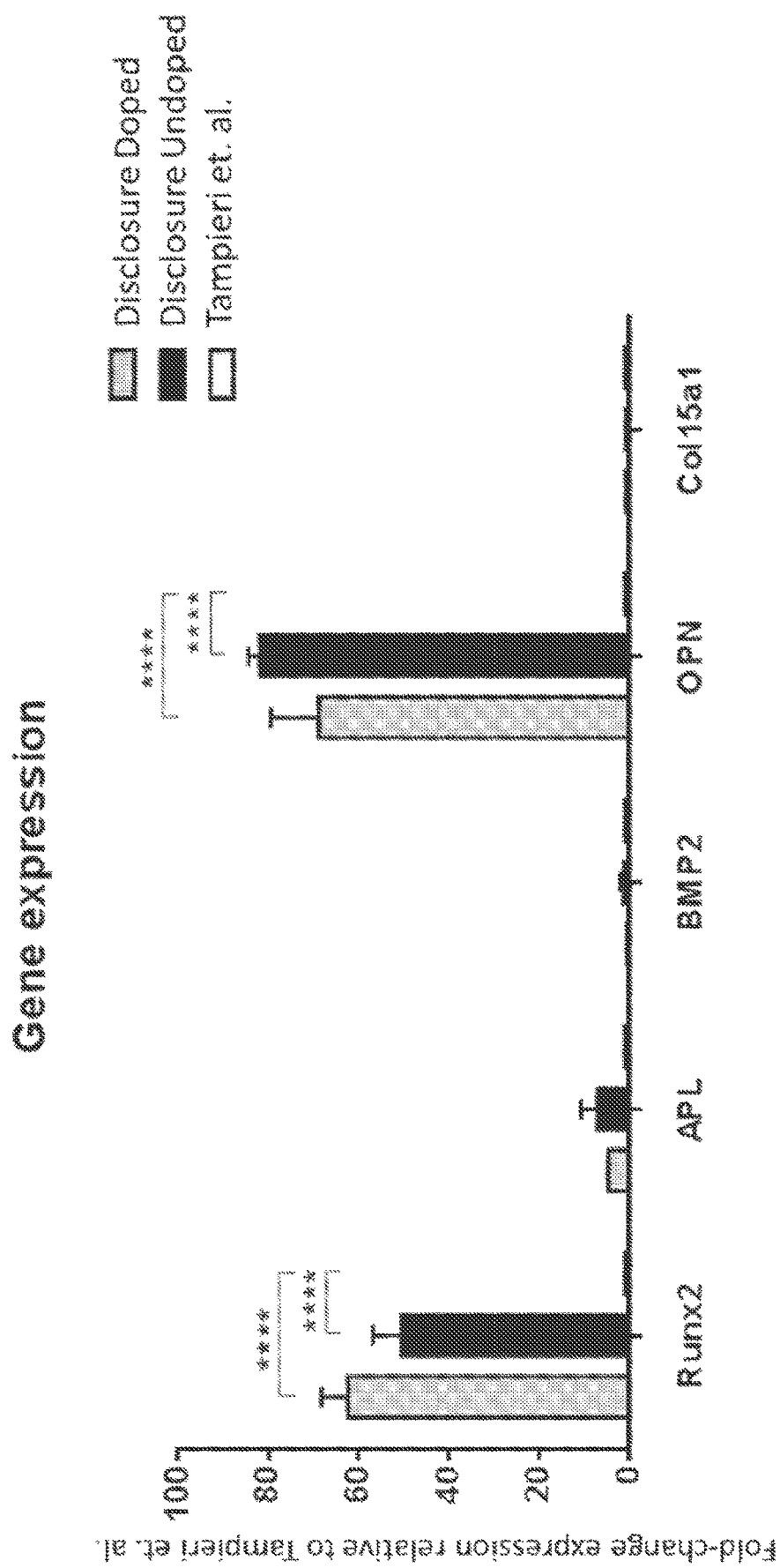
FIG. 23 shows the relative quantification ($2^{-\Delta\Delta Ct}$) of gene expression with respect to the expression of the not-doped prior art scaffold used as calibrator, after 14 days of mMSCs 3D cultured in dynamic condition with all the tested samples.
Figure 24:
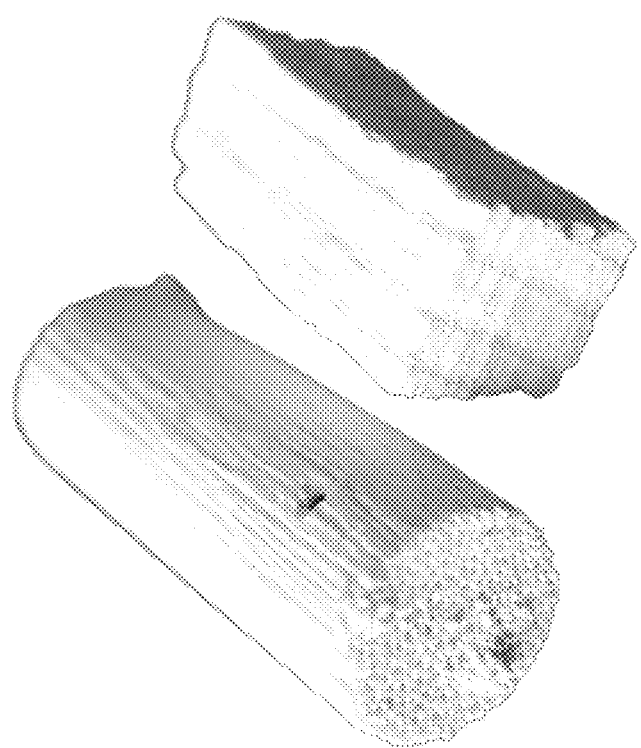
FIG. 24 shows an embodiment of the biomorphic scaffold with cuboid shape.
Figure 25:
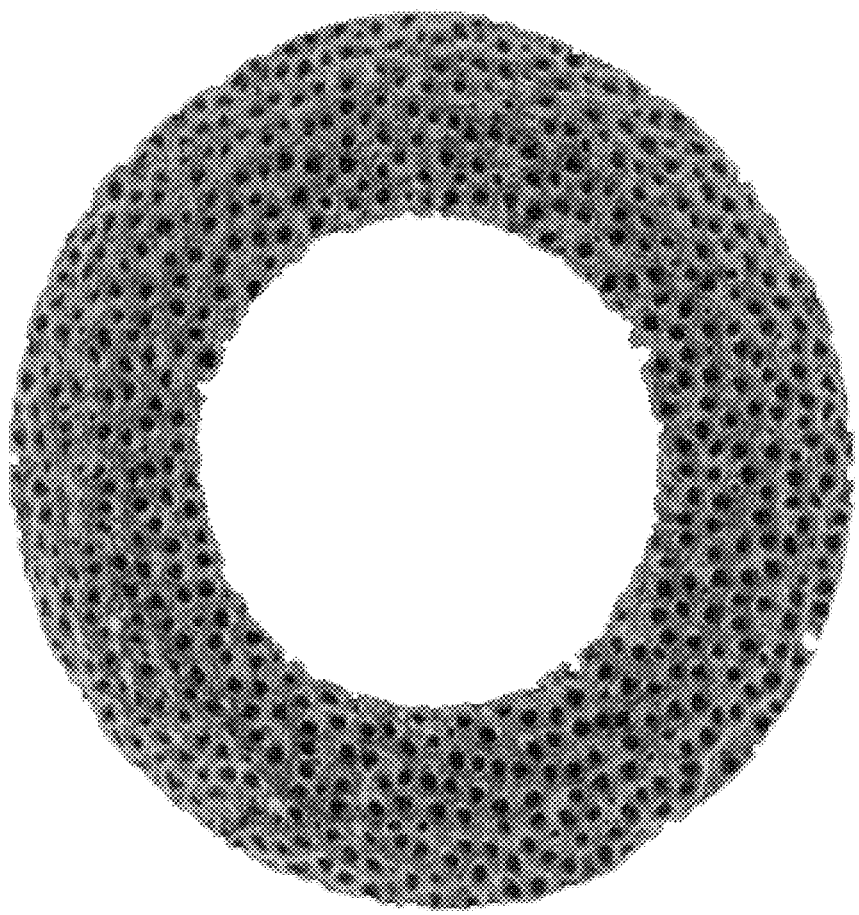
FIG. 25 shows that the channel-like structure of the biomorphic hydroxyapatite scaffold obtained with the process of the present disclosure is uniquely characterized by pervious large channels (100-300 micron in diameter) (micro CT Scan). Such channels are permissive to the formation of suitable blood vessels supporting bone regeneration.
Figure 25:
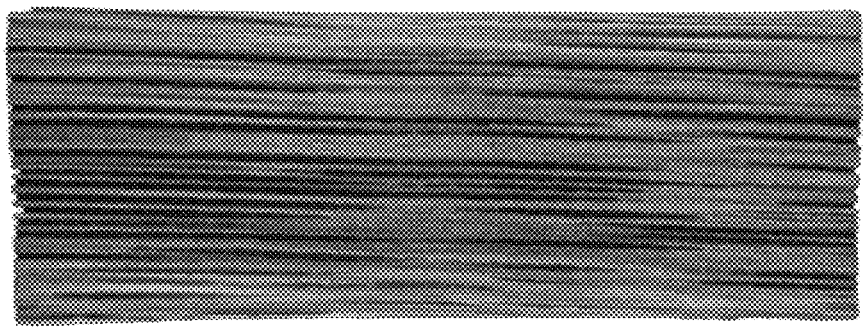

FIG. 23 shows the relative quantification ($2^{-\Delta\Delta Ct}$) of gene expression with respect to the expression of the not-doped prior art scaffold used as calibrator, after 14 days of mMSCs 3D cultured in dynamic condition with all the tested samples. Average and standard error of three samples were indicated. Statistical analysis was made by two-way ANOVA, followed by Bonferroni's post-hoc test and significant difference is indicated in the graph: ****$p \leq 0.0001$.

From the above tests, it is possible to assert that the disclosure scaffolds show a higher inductive power on the expression of osteogenic related genes, with respect to the prior art scaffolds.

REFERENCES

[1] Arch Oral Biol. 2013 January; 58(1):42-9. doi: 10.1016/j.archoralbio.2012.07.010. Epub 2012 Aug. 9. Leader genes in osteogenesis: a theoretical study. Orlando B, Giacomelli L, Ricci M, Barone A, Covani U.

[2] J Cell Physiol. 2012 August; 227(8):3151-61. doi: 10.1002/jcp.24001. Extracellular calcium chronically induced human osteoblasts effects: specific modulation of osteocalcin and collagen type XV. Gabusi E, Manlerdini C, Grassi F, Piacentini A, Cattini L, Filardo G, Lambertini E, Piva R, Zini N, Facchini A, Lisignoli G.

The invention claimed is:

1. A method of treating of a human or animal bone having a bone defect, comprising the steps of:
providing a bone substitute comprising a biomorphic hydroxyapatite scaffold obtained from a wood having a total porosity of at least 20%, said porosity being measured after subjecting the wood to a step of pyrolysis, said scaffold having a length, measured along a direction in which a dimension of the scaffold is maximum, greater than or equal to 2 cm, wherein the bone substitute has a shape that corresponds to the shape of a bone defect;
implanting the bone substitute in the bone defect of the patient.

2. The method according to claim 1, further comprising the steps of providing a 3D model of the bone defect and, based on the 3D model obtained, imparting to the scaffold a shape corresponding to the shape of the bone defect.

3. The method of claim 1, wherein said human or animal bone is a bone subjected to mechanical loads.

4. The method of claim 1, wherein said human or animal bone is tibia, metatarsus, fibula, femur, humerus or radius.

5. The method of claim 1, wherein said human or animal bone is a cranial bone-part, a spine bone or a maxilla-facial bone-part.

6. The method of claim 1, wherein the total porosity of the wood is between 60% and 95%.

7. The method of claim 1, wherein the biomorphic hydroxyapatite scaffold has a compressive strength, measured in the longitudinal direction, greater than 5 MPa.

8. The method of claim 1, wherein the biomorphic hydroxyapatite scaffold has a hierarchically organized pore structure derived from the hierarchically organized pore structure of the wood from which it is obtained.

9. The method of claim 1, wherein the wood is selected from the group consisting of rattan, pine, abachi, balsa, sipo, oak, rosewood, kempas and walnut wood.

10. The method of claim 1, wherein the hierarchically organized pore structure includes between 30 and 80%, of the total porosity, of pores having a diameter below 150 μm, the reminder to 100% of total porosity being pores having diameter greater than 150 μm.

11. The method of claim 1, wherein the wood is rattan, and between 30% and 60% of the total porosity of the scaffold is due to pores having a diameter≤10 μm.

12. The method of claim 1, wherein the wood is rattan, and at least 25% of the total porosity of the total porosity of the scaffold is due to pores having a diameter≤1 μm.

13. The method of claim 1, wherein the wood is rattan, and at least 20% of the total porosity of the scaffold is due to pores that have diameter≥150 μm.

14. The method of claim 1, wherein the biomorphic hydroxyapatite scaffold has a specific surface area (SSA)>9 m2/g.

15. The method of claim 1, wherein the hydroxyapatite is partially substituted with one or more ions selected from the group consisting of magnesium, strontium, silicon, carbonate, sodium, potassium, silver, gallium and copper.

16. A method of treating of a human or animal bone having a bone defect, comprising the steps of:

providing a bone substitute comprising a biomorphic hydroxyapatite scaffold obtained from a wood having a total porosity of between 60% and 95%, said porosity being measured after subjecting the wood to a step of pyrolysis, wherein said hydroxyapatite comprises a hierarchically organized pore structure and a compressive strength, measured along the longitudinal direction, greater than 5 MPa, wherein the bone substitute has a shape that corresponds to the shape of a bone defect;

implanting the bone substitute in the bone defect of the patient.

\* \* \* \* \*